(12) United States Patent
Stupp

(10) Patent No.: US 12,002,545 B2
(45) Date of Patent: Jun. 4, 2024

(54) TECHNIQUE FOR IDENTIFYING FEATURES

(71) Applicant: ExSano, Inc., Foster City, CA (US)

(72) Inventor: Steven Elliot Stupp, San Carlos, CA (US)

(73) Assignee: Exsano, Inc., Foster City, CA (US)

( * ) Notice: Subject to any disclaimer, the term of this patent is extended or adjusted under 35 U.S.C. 154(b) by 1331 days.

(21) Appl. No.: 15/898,543

(22) Filed: Feb. 17, 2018

(65) Prior Publication Data

US 2018/0181704 A1    Jun. 28, 2018

Related U.S. Application Data

(63) Continuation-in-part of application No. 13/507,888, filed on Aug. 2, 2012, now Pat. No. 9,898,687.

(60) Provisional application No. 61/574,555, filed on Aug. 3, 2011.

(51) Int. Cl.
| | | |
|---|---|---|
| G16B 20/20 | (2019.01) | |
| G16B 20/00 | (2019.01) | |
| G16B 40/00 | (2019.01) | |
| G16B 40/20 | (2019.01) | |
| G16B 40/30 | (2019.01) | |

(52) U.S. Cl.
CPC ............ *G16B 20/20* (2019.02); *G16B 20/00* (2019.02); *G16B 40/00* (2019.02); *G16B 40/20* (2019.02); *G16B 40/30* (2019.02)

(58) Field of Classification Search
None
See application file for complete search history.

(56) References Cited

U.S. PATENT DOCUMENTS 7,451,083 B2 *   11/2008   Frey .................. G10L 15/02
                                                 704/251

OTHER PUBLICATIONS

Schaid et al. (American Journal of Human Genetics (2002) vol. 70:425-434) (Year: 2002).*

* cited by examiner

*Primary Examiner* — Lori A. Clow
(74) *Attorney, Agent, or Firm* — Steven Stupp

(57) ABSTRACT

During a feature-selection technique, an electronic device calculates combinations of features and noise vectors, where a given combination corresponds to a given feature and a given noise vector. Then, the electronic device determines statistical associations between information specifying types of events and the combinations, where a given statistical association corresponds to the types of events and a given combination. Moreover, the electronic device identifies a noise threshold associated with the combinations. Next, for a group of combinations having statistical associations equal to or greater than the noise threshold, the electronic device selects a subset of the features based at least in part on a first aggregate property of the group of combinations, where the first aggregate property comprises numbers of occurrences of the features in the group of combinations.

20 Claims, 12 Drawing Sheets

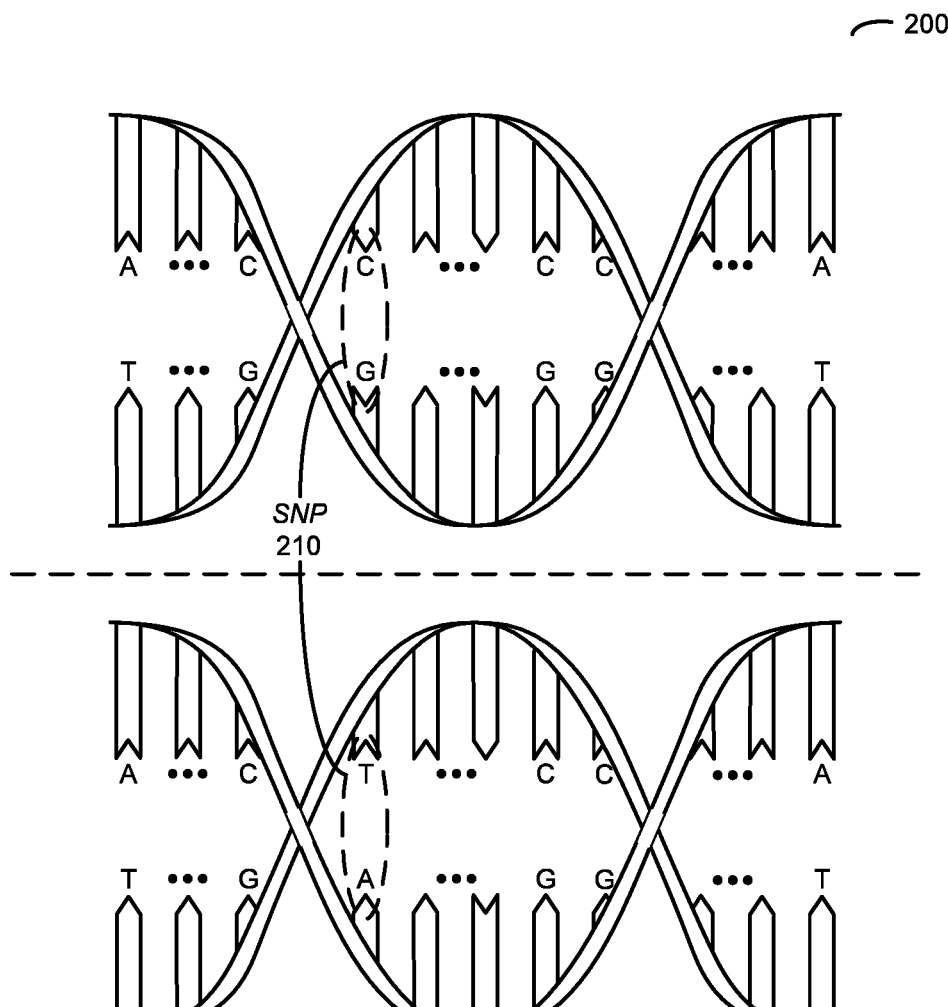

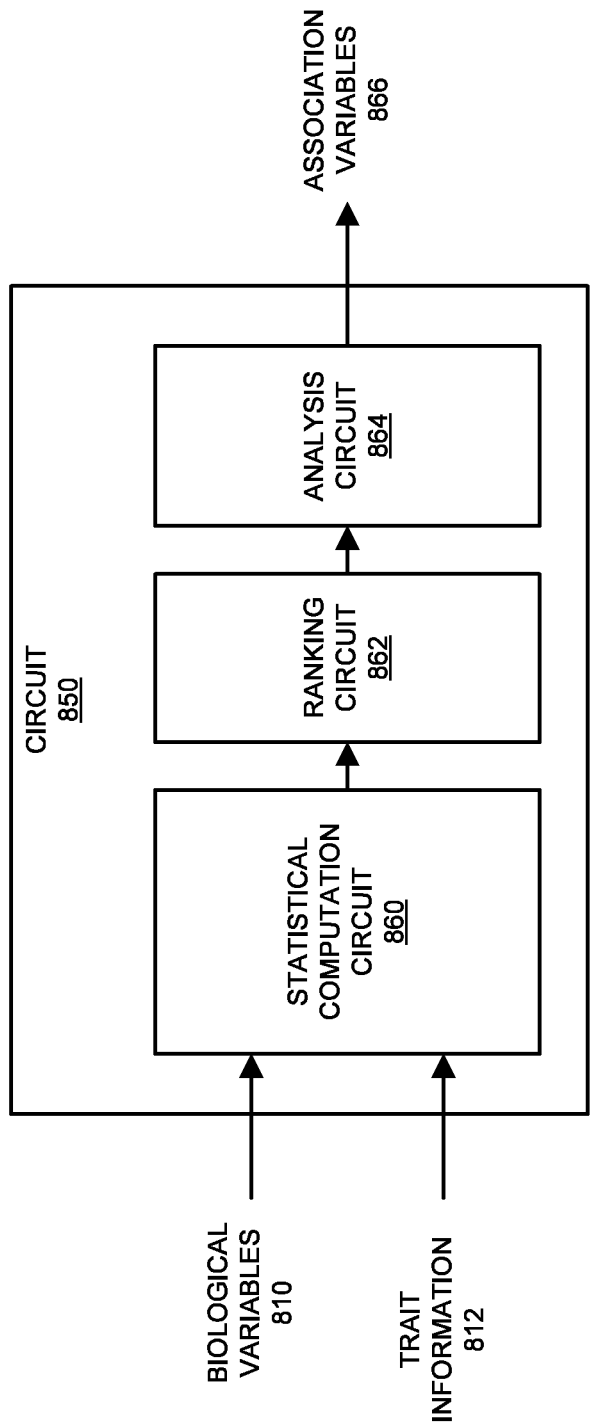

TECHNIQUE FOR IDENTIFYING FEATURES

CROSS REFERENCE TO RELATED APPLICATIONS

This application claims priority under 35 U.S.C. 120 as a Continuation-in-Part of U.S. patent application Ser. No. 13/507,888, "Technique for Identifying Association Variables," filed on Aug. 2, 2012, and claims priority under 35 U.S.C. 119(e) to U.S. Provisional Application Ser. No. 61/574,555, "Technique for Identifying Association Variables," filed on Aug. 3, 2011, the contents of both of which are herein incorporated by reference.

This application is also related to U.S. patent application Ser. No. 12/456,561, "Technique for Identifying Association Variables," filed on Jun. 18, 2009 (now U.S. Pat. No. 8,639,446), and to U.S. patent application Ser. No. 13/573,888, "Technique for Identifying Association Variables," filed on Oct. 11, 2012 (now U.S. Pat. No. 9,898,687).

FIELD

The present disclosure relates generally to an apparatus, and related methods, for processing data, and more specifically, for identifying genetic features that are associated with a trait.

BACKGROUND

Many mathematical problems involve analyzing data to determine relationships between variables. For example, in regression analysis an expression can be determined to describe data (which is sometimes referred to as 'fitting' the expression to the data). This is shown in FIG. 1A, which presents a drawing 100 illustrating the fitting a line to data. The equation for a line y (the independent variable) can be expressed as $$y=mx+b,$$

where x (the data) is the dependent variable, and m and b are unknown coefficients (the slope and y-intercept, respectively) that are to be determined during the fitting. In this example, each datum in the data corresponds to a point in the x-y plane (such as $x_0$, $y_0$).

Typically, the minimum number of data points needed to uniquely determine the fitting equation equals the number of unknowns in the fitting equation (as shown in FIG. 1A, for a line, the minimum number of data points is two). If there are more data points than this minimum number, statistical techniques such as least-squares regression may be used to determine the unknown coefficients. However, if there are fewer data points available than the minimum number, it is typically not possible to uniquely determine the unknowns. This is shown in FIG. 1B, which presents a drawing 150 illustrating the fitting of multiple lines to a datum. In principle, there are an infinite number of equivalent fitting solutions that can be determined. This type of problem is sometimes referred to as 'sparse' or 'underdetermined.'

Unfortunately, many interesting problems are underdetermined. For example, in biology, important differences between different individual's genomes can be described by single nucleotide polymorphisms (SNPs). As shown in FIG. 2, which presents a drawing 200 illustrating a SNP 210, a SNP is a deoxyribonucleic-acid (DNA) sequence variation that occurs when a single nucleotide, such as adenine (A), thymine (T), cytosine (C), or guanine (G), in a chromatid in the genome (or another shared sequence) differs between members of a species (or between paired chromosomes in an individual). For example, two sequenced DNA fragments from different individuals, AA . . . CT . . . CA . . . A to AA . . . TT . . . CA . . . A, contain a difference in a single nucleotide (in this case, there are two alleles, C and T). Variations in the DNA sequences of humans can affect how humans develop diseases and respond to pathogens, chemicals, drugs, vaccines, and other agents. Consequently, there is great interest in identifying associations between SNPs and the expression of such traits or phenotype information in a population of individuals, such as matched cohorts with and without a disease.

However, even after eliminating correlated SNPs using a haplotype map (which includes information about closely related alleles that are inherited as a unit), there may still be several hundred thousand or more SNPs for each individual in a population. In order to identify the associations, these SNPs may be compared to the expression of a trait in the population, such as the occurrence of a disease. Typically, the population may include several thousand individuals. Consequently, identifying the associations involves 'fitting' several hundred thousand SNPs (the fitting space) to several thousand data points, which is an extremely underdetermined problem that increases the complexity, time and expense when trying to identify the associations.

Furthermore, it is unusual for a disease (or, more generally, an expressed trait) to be associated with a single gene. More typically, the disease is associated with multiple genes (i.e., it is polygenetic), as well as one or more environmental factors. In the case of SNPs, including these additional variables and/or combinations of variables causes a power-law increase in the size of the fitting space. If the population size (several thousand people) remains unchanged, the problem becomes vastly underdetermined. Unfortunately, increasing the size of the population is often difficult because of the associated expense and time needed to obtain biological samples.

Therefore, there is a need for an analysis technique to identify associations in underdetermined problems without the problems listed above.

SUMMARY

A first group of embodiments of the present disclosure describes a feature-selection technique. In this feature-selection technique, an apparatus, such as a computer system or a circuit, accesses (e.g., in a computer-readable memory) a set of genetic features for individuals in a group of individuals, a set of noise vectors for the individuals and associated trait information, where a number of genetic features may be larger than a number of individuals. Then, the computer system determines statistical associations between combinations of the genetic features and the noise vectors for the individuals in the group and the trait information, where a given combination corresponds to a given genetic feature and a given noise vector. Moreover, the computer system selects a subset of genetic features in the set of genetic features based on one or more aggregate properties of at least a subset of the combinations, where the one or more aggregate properties include numbers of occurrences of the genetic features in at least the subset of the combinations. Note that a number of combinations may be larger than the number of genetic features, the selecting may involve an underdetermined problem in which a ratio of the number of the combinations to the number of the individuals is larger than a predefined value and p-values associated with the selected subset of genetic features may be less than a second predefined value.

Moreover, the one or more operations may include providing a predictive model based at least on the subset of genetic features, the trait information and a supervised-learning technique, where the predictive model provides a recommendation or a recommendation value for a therapeutic intervention for an individual based on at least some of the subset of genetic features.

Furthermore, the one or more operations may include generating the combinations of the genetic features and the noise vectors for the individuals in the group. For example, the generating may involve a set of mathematical operations, which may include nonlinear mathematical operations. Note that the one or more aggregate properties may include numbers of occurrences of mathematical operations in the set of mathematical operations.

Additionally, the one or more operations may include identifying a noise floor, where the subset of genetic features is included in the combinations above the noise floor. For example, the noise floor may be identified based on the one or more aggregate properties of different subsets of the combinations. However, other techniques may be used to identify the noise floor.

In some embodiments, the subset of the combinations includes the combinations having N largest statistical associations, where N is an integer.

Moreover, the supervised-learning technique may include one or more of: a kernel method, a least absolute shrinkage and selection operator (LASSO), logistic regression, ridge regression, a regression technique, a classification technique, a Bayesian technique, and a neural network.

Furthermore, the set of genetic features may include one or more of: genetic features associated with deoxyribonucleic acid, genetic features associated with ribonucleic acid, genetic features associated with epigenetic information, genetic features associated with one or more proteins, and another type of biological marker.

Note that the predefined value may be 1000 and/or the second predefined value may be $10^{-10}$. Additionally, the second predefined value may be less than a p-value that includes a Bonferroni correction that is based on the number of combinations.

In some embodiments, the noise vectors include pseudorandom or random values with an amplitude that is based on a statistical characteristic of the set of genetic features.

Moreover, in some embodiments, the feature-selection technique is applied to another type of data than the set of genetic features. This may include another type of medical data (such as environmental data or an electronic-medical record) or a non-medical dataset.

In some embodiments, the feature-selection technique is, at least in part, performed by a cloud-based computer, and at least some of the operations in the feature-selection technique are performed by a local client.

Another embodiment provides a method that includes at least some of the operations performed by the computer system.

Another embodiment provides a computer-program product for use with the apparatus. This computer-program product includes instructions for at least some of the operations performed by the computer system.

A second group of embodiments describes an electronic device, such as a computer system or a circuit, that selects a subset of features. This electronic device calculates combinations of features and noise vectors, where a given combination corresponds to a given feature and a given noise vector. Then, the electronic device determines statistical associations between information specifying types of events and the combinations, where a given statistical association corresponds to the types of events and a given combination. Moreover, the electronic device identifies a noise threshold associated with the combinations (e.g., as an ensemble or as a group). Next, for a group of combinations having statistical associations equal to or greater than the noise threshold, the electronic device selects the subset of the features based at least in part on a first aggregate property of the group of combinations, where the first aggregate property includes numbers of occurrences of the features in the group of combinations.

For example, the combinations may be determined based at least in part on mathematical operations, where the given combination is based at least in part on a given mathematical operation. In some embodiments, the subset of the features is selected based at least in part on a second aggregate property, where the second aggregate property includes numbers of occurrences of the mathematical operations for the features in the group of combinations.

Moreover, the features may include at least one of: genetic features, environmental features, features associated with one or more electronic medical records, or features associated with insurance records. In some embodiments, the genetic features include at least one of: features associated with deoxyribonucleic acid, features associated with ribonucleic acid, features associated with epigenetic information, features associated with one or more proteins, or features associated with another type of biological marker.

Furthermore, the types of events may include occurrence and absence of an event. Alternatively or additionally, the types of events may include at least one or more of: occurrence and absence of a trait, different medical outcomes, responses to a first type of treatment, states of an episodic medical condition, or costs associated with a second type of treatment.

Additionally, the noise threshold may be identified based at least in part on at least one of: stability of rankings associated with at least a pair of subsets of the combinations having statistical associations equal to or greater than the noise threshold, in which a given ranking is based at least in part on a third aggregate property of the given subset of the combinations; or differences between autocorrelations and cross-correlations of the combinations having the statistical associations equal to or greater than the noise threshold. Note that the third aggregate property may be the same as or different from the first aggregate property. Thus, in some embodiments, the third aggregate property may be the first aggregate property.

Moreover, the features may be associated with one of: an individual, or a group of individuals.

Furthermore, the noise vectors may include random or pseudorandom numbers having mean amplitudes corresponding to a statistical characteristic of the features.

Additionally, mean frequencies of occurrence of categorical variables in the noise vectors may approximately match (such as within 1, 5 or 10% of) mean frequencies of occurrence of the categorical variables in the features.

In some embodiments, the electronic device generates a predictive model based at least in part on the subset of features, the types of events and a supervised-learning technique. The predictive model may provide a recommendation or a prediction based at least in part on values for the subset of the features.

Note that the features may include medical data or non-medical data.

In some embodiments, at least some of the operations performed by the electronic device are performed by a cloud-based computer, and at least some of the operations performed by the electronic device are performed by a local client.

Another embodiment provides a method that includes at least some of the operations performed by the electronic device.

Another embodiment provides a computer-program product for use with the electronic device. This computer-program product includes instructions for at least some of the operations performed by the electronic device.

A third group of embodiments describes an apparatus, such as a computer system or a circuit, that identifies one or more association variables that are associated with a trait. This apparatus may determine patterns of occurrence of compound variables based on a set of mathematical interactions and patterns of occurrence of a set of biological variables of a group of life forms (such as humans, animals, bacteria, fungi and/or plants), where a pattern of occurrence of a given compound variable may be determined based on a given mathematical interaction in the set of mathematical interactions and patterns of occurrence of a given pair of biological variables in the set of biological variables. Moreover, the apparatus may calculate statistical relationships corresponding to a pattern of occurrence of the trait in the group of life forms and the patterns of occurrence of the compound variables. Note that a given statistical relationship corresponds to the pattern of occurrence of the trait in the group of life forms and a pattern of occurrence of a given compound variable, and the calculation may include contributions from presence and absence information in the patterns of occurrence of the trait and the pattern of occurrence of the given compound variable.

Using the statistical relationships, the apparatus may determine numbers of occurrences of biological variables that were used to determine the compound variables in at least a subset of the compound variables, where the subset of the compound variables have statistical relationships greater than a statistical confidence value. Furthermore, the apparatus may determine numbers of different mathematical interactions used to determine the compound variables in the subset of the compound variables for the biological variables that are associated with the corresponding numbers of occurrences. Then, the apparatus may identify one or more of the biological variables in the set of biological variables as the one or more association variables based on the numbers of occurrences and/or the numbers of different mathematical interactions.

In some embodiments, the given compound variable is determined by performing a mathematical operation specified by the given mathematical interaction on corresponding entries in a pattern of occurrence of a first biological variable in the given pair of biological variables and a pattern of occurrence of the second biological variable in the given pair of biological variables.

Moreover, the calculating may involve a non-parametric statistical analysis technique, such as: a chi-square analysis technique, a log-likelihood ratio analysis technique, a goodness-of-fit (G-test) technique, and/or a Fisher's exact probability analysis technique. More generally, the calculating may involve a supervised learning technique. This supervised learning technique may include a support vector machines (SVM) analysis technique and/or a classification and regression tree (CART) analysis technique.

Note that the statistical confidence value may correspond to a statistical significance value associated with the statistical relationships. For example, the statistical confidence value may correspond to a noise floor in the statistical relationships. This noise floor may be determined based on approximate stability of at least a portion of a ranking of the biological variables that were used to determine compound variables in at least a subset of the compound variables, where the ranking is based on the numbers of occurrences of the biological variables. Moreover, the approximate stability may be for statistical confidence values between the statistical confidence value and another statistical confidence value, where the other statistical confidence value corresponds to a larger statistical significance value associated with the statistical relationships than the statistical confidence value. However, another technique may be used to identify the noise floor.

In some embodiments, the apparatus calculates additional statistical relationships corresponding to a pattern of occurrence of a sequence of values and the patterns of occurrence of the compound variables, where a given additional statistical relationship corresponds to the pattern of occurrence of the sequence of values and the pattern of occurrence of the given compound variable. This calculation may include contributions from presence and absence information in the patterns of occurrence of the sequence of values and the pattern of occurrence of the given compound variable. Then, the apparatus determines additional numbers of occurrences of biological variables that were used to determine additional compound variables in at least another subset of the compound variables, where the other subset of the compound variables have statistical relationships greater than the statistical confidence value or another statistical confidence value. Moreover, the apparatus corrects the numbers of occurrences of biological variables based on the additional numbers of occurrences of biological variables prior to identifying the one or more association variables. Note that the sequence of values includes a random or a pseudorandom sequence of values, and a number of entries in the sequence of values may equal a number of life forms in the group of life forms.

The set of biological variables may include information associated with at least single nucleotide polymorphisms (SNPs) and/or copy number variations (CNVs). More generally, the set of biological variables may include epigenetic information, information associated with deoxyribonucleic acid, information associated with ribonucleic acid, information associated with one or more proteins, and/or information associated with another biological marker. In some embodiments, the set of biological variables includes one or more environmental factors. Note that the trait may include phenotype information, such as that for a disease and, more generally, for a characteristic.

Furthermore, a given pattern of occurrence of a given variable, which can include the trait in the group of life forms, the given compound variable, or either one of the given pair of biological variables, may include presence and absence information of the given variable. For example, the presence information of the given variable may include expression or suppression of the given variable, and the absence information of the given variable includes an absence of expression or an absence of suppression of the given variable.

In some embodiments, the apparatus excludes at least some of the compound variables prior to calculating the statistical relationships. Note that a given excluded compound variable may have a number of presences or absences in the pattern of occurrence of the given excluded compound variable that is greater than a first value or less than a second value.

The set of biological variables may include categorical data. Alternatively, the apparatus may convert the set of biological variables into categorical data prior to calculating the compound variables. Note that the converting for a given genetic locus (such as a base-pair location) may be based on a minor allele frequency and/or a major allele frequency of a SNP at the given genetic locus. Additionally, the apparatus may exclude at least some of the biological variables in the set of biological variables prior to calculating the compound variables. Note that a given excluded biological variable may have a number of presences or absences in the pattern of occurrence of the given excluded biological variable that is greater than a third value or less than a fourth value.

In some embodiments, the apparatus determines the set of biological variables of the group of life forms based on biological samples associated with the group of life forms.

Note that identifying the one or more association variables may constitute an underdetermined problem. For example, a number of life forms in the group of life forms may be significantly less than a number of biological variables in the set of biological variables.

Moreover, in some embodiments, the apparatus analyzes another type of data than the set of biological variables. This may include another type of medical data (such as environmental data or an electronic-medical record) or a non-medical dataset.

In some embodiments, at least some of the operations performed by the apparatus are performed by a cloud-based computer, and at least some of the operations performed by the apparatus are performed by a local client.

Another embodiment provides a method that includes at least some of the operations performed by the apparatus.

Another embodiment provides a computer-program product for use with the apparatus. This computer-program product includes instructions for at least some of the operations performed by the apparatus.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE DRAWINGS

FIG. 2 is a drawing illustrating a single nucleotide polymorphism (SNP) at a single base-pair location.

FIG. 3 is a drawing illustrating conversion of biological variables into categorical data in accordance with an embodiment of the present disclosure.

FIG. 8B is a block diagram illustrating a circuit in accordance with an embodiment of the present disclosure.

Figure 1A:
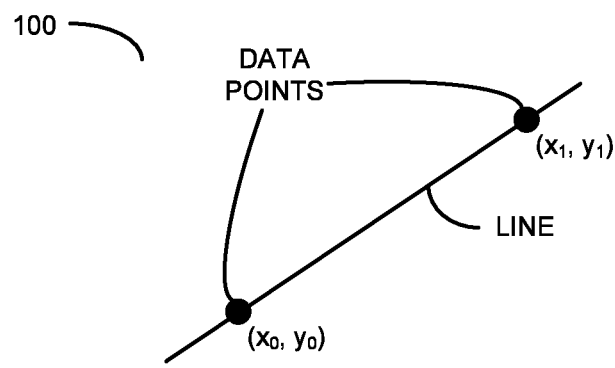
FIG. 1A is a drawing illustrating fitting a line to data.
Figure 1B:
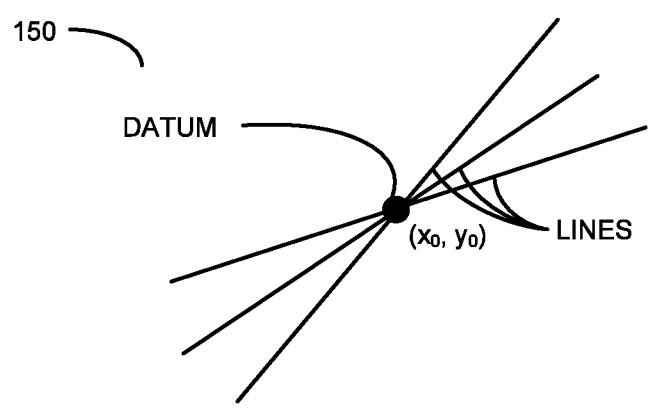
FIG. 1B is a drawing illustrating fitting multiple lines to a datum.

Table 1 provides identified association variables in an exemplary embodiment.

Table 2 provides a contingency table in an exemplary embodiment.

Note that like reference numerals refer to corresponding parts throughout the drawings. Moreover, multiple instances of the same part are designated by a common prefix separated from an instance number by a dash.

DETAILED DESCRIPTION

Embodiments of an apparatus (such as a computer system or a circuit), a method (which is sometimes referred to as an 'identification technique,' a 'feature-extraction technique' or a feature-selection technique'), and a computer-program product (e.g., software) for use with the apparatus are described. During the feature-selection technique, a computer system accesses a set of genetic features for individuals in a group of individuals, a set of noise vectors for the individuals and associated trait information, where a number of genetic features may be larger than a number of individuals. Then, the computer system determines statistical associations between combinations of the genetic features and the noise vectors for the individuals in the group and the trait information, where a given combination corresponds to a given genetic feature and a given noise vector. Moreover, the computer system selects a subset of genetic features in the set of genetic features based on one or more aggregate properties of at least a subset of the combinations, where the one or more aggregate properties include numbers of occurrences of the genetic features in the at least the subset of the combinations. Note that a number of combinations may be larger than the number of genetic features, the selecting may involve an underdetermined problem in which a ratio of the number of the combinations to the number of the individuals is larger than a predefined value and p-values associated with the selected subset of genetic features are less than a second predefined value.

In some embodiments, an apparatus may be used to identify one or more association variables that are associated with a trait. In particular, compound variables may be determined for biological variables in a set of biological variables of a group of life forms (such as genetic data for a group of people, animals, bacteria, fungi and/or plants) based on a set of mathematical interactions. (Alternatively, the compound variables may be pre-determined.) A given compound variable may be determined using a given mathematical interaction and one or more biological variables (such as a given pair of biological variables), where a given entry in the compound variable for a given one of the life forms is based on a presence or absence of the one or more biological variables for the given one of the life forms. For example, the given entry may be determined by performing a logical operation (AND, OR, NOT, XOR and/or another Boolean operation) or a mathematical operation specified by the given mathematical interaction on the values of one or more biological variables of the given life form. Alternatively or additionally, the given entry in the compound variable for the given one of the life forms may be based on an expression or suppression of one or more biological variables for the given one of the life forms.

Then, the apparatus may calculate statistical relationships between a pattern of occurrence of the trait associated with a group of life forms (e.g., presence or absence of the trait in the group of life forms) with patterns of occurrence of compound variables in the set of biological variables of the group of life forms (e.g., presence or absence entries in the compound variables). These calculations may involve a non-parametric statistical analysis technique and/or a supervised learning technique.

Next, the apparatus may determine numbers of occurrences of biological variables that were used to determine compound variables in at least a subset of the compound variables that have statistical relationships greater than a statistical significance value, which may correspond to a noise floor in the statistical relationships. This noise floor may be determined based on approximate stability of at least a portion of an occurrence ranking based on the numbers of occurrences for statistical confidence values between the statistical confidence value and another statistical confidence value, i.e., a range of statistical confidence values. However, another technique may be used to identify the noise floor, such as based on a difference between an autocorrelation and a cross-correlation of the biological variables.

Moreover, the apparatus may determine numbers of different mathematical interactions that were used to determine the compound variables in the subset of the compound variables for the biological variables that are associated with the corresponding numbers of occurrences.

Furthermore, the apparatus may identify one or more of the biological variables as one or more association variables based on the numbers of occurrences and/or the numbers of different mathematical interactions. For example, N association variables may be the top-N values in rankings based on the numbers of occurrences and/or the numbers of different mathematical interactions.

In some embodiments, the apparatus performs a correction for a background prior to identifying the one or more association variables. For example, the apparatus may subtract from the occurrence ranking another occurrence ranking which is associated with numbers of occurrences of the biological variables that were used to determine compound variables in other statistically significant statistical relationships (i.e., those compound variables which have statistical relationship values greater than the same or another statistical significance value) between the patterns of occurrence of the compound variables and a pattern of occurrence of a sequence of values (such as a random or a pseudo-random sequence of values). However, in some embodiments, another technique may be used to correct for the background, such as determining the statistical associations based on the expected values associated with the mathematical operations if the biological variables are assumed to be random variables having statistical moments matching those of the set of biological variables.

In the discussion that follows, the following definitions are used:

the meaning of 'configured' may include 'to set up for operation especially in a particular way', such as a circuit configured for a particular function or a program configured to be executed on a particular processor or computer;

the meaning of 'configurable' may include 'capable of being configured in a particular way', such as a programmable circuit that is configurable or a program (source code or compiled) that can be configured to executed on the particular processor at run time;

the meaning of 'based on' may include 'is a function of', 'using' and/or 'according to';

the meaning of 'group of life forms' may include 'a group that includes one or more people, animals, bacteria, fungi, plants and/or an engineered life form (such as a genetically engineered life form);

the meaning of 'pattern of occurrence of a variable or a trait for a group of life forms' may include 'values corresponding to presence and/or absence information for the variable or the trait for each of the life forms in the group', 'values corresponding to expression and/or non-expression information for the variable or the trait for each of the life forms in the group', 'values corresponding to suppression and/or non-suppression information for the variable or the trait for each of the life forms in the group', and/or 'values corresponding to expression and/or suppression information for the variable or the trait for each of the life forms in the group' (note that non-expression or non-suppression may be equivalent and may correspond to a value between expression and suppression);

the meaning of 'ranking' may include 'a listing of items in a group according to a system of rating';

the meaning of 'allele' may include two or more alternative forms of a genetic locus, where a single allele for each genetic locus may be inherited separately from each parent (e.g., at a genetic locus for eye color an allele might result in blue or brown eyes);

the meaning of 'phenotype' may include 'the observable traits or characteristics of an organism, such as hair color, weight, or the presence or absence of a disease, which may not be genetic or may not be solely genetic';

the meaning of 'epigenetic' may include 'something that affects a cell, organ, plant, animal or individual (i.e., a human) without directly affecting its DNA, which may indirectly influence the expression of the genome'; and the meaning of 'disease' may include 'an illness or sickness characterized by an impairment of health or a condition of abnormal functioning'.

In general, the trait includes phenotype information, such as: how life forms (for example, humans) develop diseases and respond to pathogens, chemicals, drugs (or pharmacological agents), vaccines, and/or other agents. In some embodiments, the trait includes a disease. This disease may include: a type of cancer, an auto-immune disease, an immune-related disease, a form of arthritis, a disease of at least a portion of the endocrine system, a metabolic disease, cardiovascular disease, a neurological disease, a respiratory disease, joint disease, gastrointestinal disease, a disease of a component in blood, a psychological disease or mental illness, asthma, an allergy, an inflammatory disease, a disease involving a histamine response, a type of skin disease, a circadian rhythm disorder a degenerative disease, a chronic disease, and/or an episodic disease. For example, the disease may include: rheumatoid arthritis, lupus, thyroid disease, gout, diabetes, chronic fatigue syndrome, insomnia, depression, anxiety, bipolar disorder, colitis, ulcerative colitis, inflammatory bowel disease, Crohn's disease, candida, celiac disease, hepatitis, irritable bowel syndrome, one or more food allergies, one or more food sensitivities, menstrual cramps, chronic pain, back pain, facial pain, fibromyalgia, asthma, migraines, abdominal migraines, cyclic vomiting syndrome, cluster headaches, chronic headaches, tension headaches, another type of headaches, seizures, epilepsy, neurodermatitis, acne, psoriasis, adiposity, hypertonia, heart disease, hypertension, arteriosclerosis, and/or acquired immune deficiency syndrome. In some embodiments, the trait may include multiple illnesses, which may or may not have an associated comorbidity. However, as noted above, in some embodiments the trait includes a characteristic, such as: intelligence, a physical attribute, a skill, longevity, etc. Thus, the trait may not be confided to a disease; instead it may include a positive or desirable attribute.

We now describe embodiments of a technique for identifying one or more association variables that are associated with a trait. In the discussion that follows, SNPs are used as an illustration of biological variables. However, in other embodiments the biological variables may include: epigenetic information (such as methylation or demethylation), information associated with DNA (such as one or more copy number variations or frame shifts), information associated with ribonucleic acid (RNA), information associated with one or more proteins (such as one or more enzymes), and/or information associated with another biological marker or type of biological marker.

Note that in some embodiments the biological variables include environmental factors, such as: environmental stimuli (for example, light or sound), weather conditions, behaviors, patterns of behaviors (when the behaviors occur or do not occur), diet (including foods or beverages consumed or not consumed), dietary patterns (when the foods or beverages are consumed or are not consumed), use of drugs (prescription or recreational), activities, exposure to chemicals, exposure to toxins, exposure to one or more fungi, and/or exposure to infectious agents (for example, bacteria, viruses, fungi, and/or prions).

Continuing the discussion of FIG. 2, SNPs may fall within coding sequences of genes, non-coding regions of genes, or in the intergenic regions between genes. Because of the degeneracy of the genetic code, SNPs within a coding sequence may not necessarily change the amino acid sequence of the protein that is produced. A SNP in which both forms lead to the same polypeptide sequence is termed 'synonymous' (sometimes called a silent mutation). However, if a different polypeptide sequence is produced they are 'non-synonymous'. Note that SNPs that are not in protein-coding regions may still have consequences for gene splicing, transcription factor binding, or the sequence of non-coding RNA.

Most common SNPs have only two alleles. It is important to note that there are variations between populations (such as between groups of humans), so a SNP allele that is common in one geographical or ethnic group (such as a given population or a given group of life forms) may be much rarer in another. Typically, in order for a variation to be considered a SNP, it occurs in at least 1% of a given population.

SNPs can be assigned a minor allele frequency, which is the lowest allele frequency at a genetic locus (such as a base-pair location) that is observed in a particular or given population. This is simply the lesser of the two allele frequencies for SNPs. Similarly, SNPs can be assigned a major allele frequency, which is the largest allele frequency at the genetic locus (such as the base-pair location) that is observed in the given population. This is simply the larger of the two allele frequencies for SNPs.

For the given population, the minor allele frequencies and/or the major allele frequencies may be used to convert a sequence of SNPs at multiple genetic loci to categorical or discrete data. In an exemplary embodiment, the categorical data includes two classes or categories, i.e., binary categorical data. This is shown in FIG. 3, which presents a drawing 300 illustrating conversion of biological variables into categorical data. In particular, SNP information is converted during conversion 314 into binary data. For example, at base-pair locations, such as base-pair location 310, SNPs having a minor allele frequency may be coded as '0's. Similarly, at the other base-par locations, SNPs having a major allele frequency may be coded as '1's.

More generally, categorical data may be represented by codes. For categorical variables having two class or categories, a single binary digit may be used, such as 0 or 1, or −1 or 1. Thus, in the case of SNPs, genetic loci corresponding to minor frequencies may be coded as −1s and genetic loci corresponding to major frequencies may be coded as 1s. Note that a wide variety of code choices may be used. Thus, considering both copies of a chromosome, the presence of two copies of a SNP at a genetic location on both copies of the chromosome having a minor allele frequency may be coded as a '0'; the presence of the SNP having the minor allele frequency at the genetic location on one of the copies and the presence of the SNP having a major allele frequency at the genetic location on the other of the copies may be coded as a '1'; and the presence of two copies of the SNP at the genetic location on both copies of the chromosome having the major allele frequency may be coded as a '2'.

Also note that, when there are more than two categories, such as A, T, C, and G for a DNA sequence, a dummy variable having K values or bits may be used. Moreover, data having qualitative or continuous values can be converted in to categorical data by partitioning using one or more thresholds. In some embodiments, different thresholds may be used for different biological variables or different types of biological variables (such as SNPs versus environmental factors). Furthermore, in some embodiments categorical data is converted into continuous values using interpolation (such as minimum bandwidth interpolation), subject to the limitations associated with the Nyquist sampling criterion.

In some embodiments, either before conversion to categorical data or after, SNP data for a given population may be windowed or reduced using a haplotype map for the given population. This windowing operation may remove SNPs at genetic loci in the data that are highly correlated with one or more other SNPs in the data. For example, many SNPs are highly spatially correlated with each other over or across one or more regions in the genomes or sequences of most or all of the given population. For each group of highly correlated SNPs in the data, all but one may be removed from the set of biological variables associated with the given population before attempting to identify the one or more association variables.

Figure 4A:
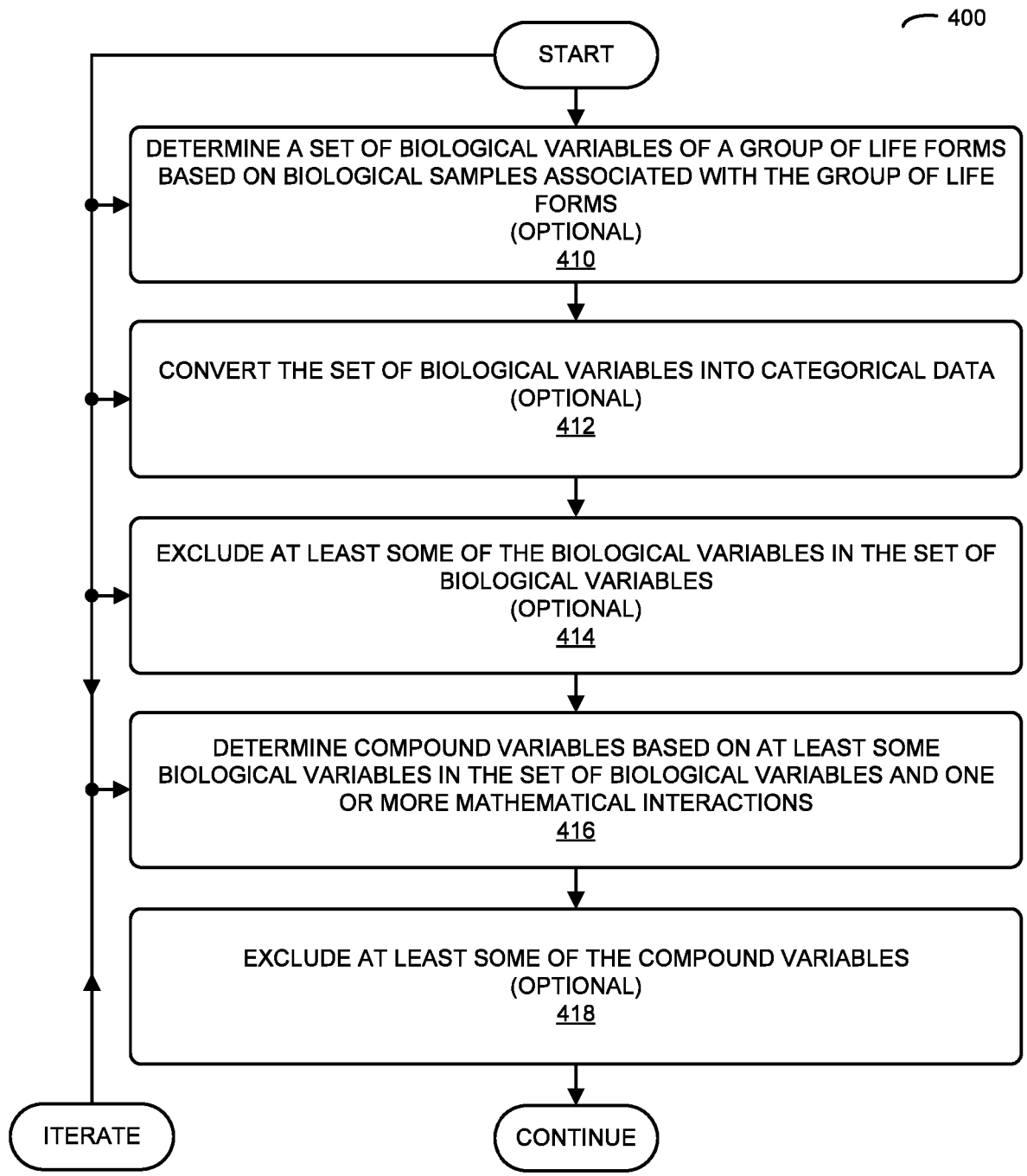
FIG. 4A is a flow chart illustrating a process for identifying one or more association variables that are associated with a trait in accordance with an embodiment of the present disclosure.
Figure 9:
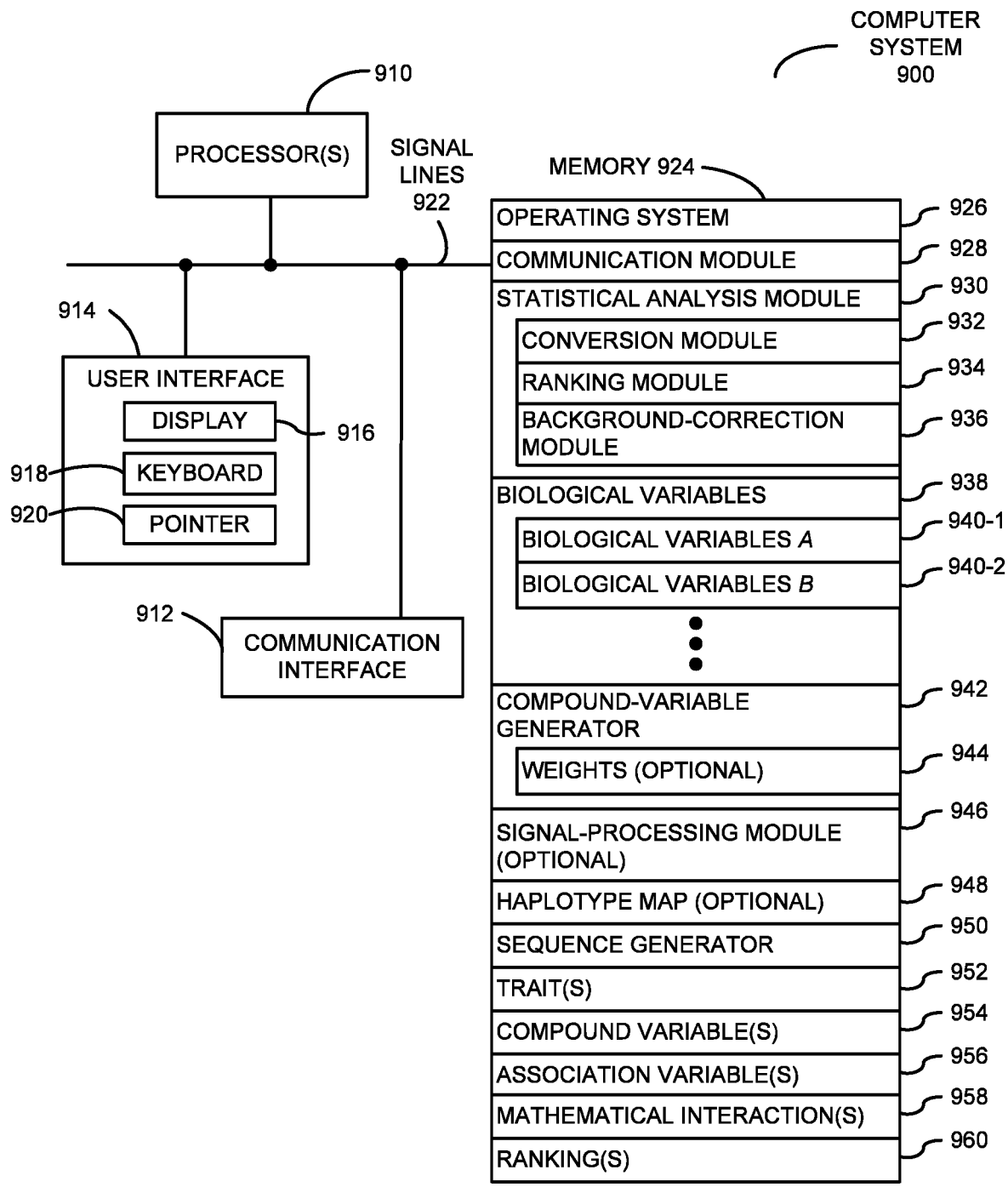
FIG. 9 is a block diagram illustrating a computer system in accordance with an embodiment of the present disclosure.

FIG. 4A presents a flow chart illustrating a process 400 for identifying one or more association variables that are associated with a trait, which may be performed by a computer system (such as computer system 900 in FIG. 9). During this process, a set of biological variables of the group of life forms is optionally determined based on biological samples associated with the group of life forms (operation 410). For example, biological variables may be determined by analyzing one or more biological samples for each member of the group of life forms, thereby determining the set of biological variables. These biological samples may include: a blood sample, a urine sample, a stool sample, a saliva sample, a sweat sample, a mucus sample, a skin scrapping, and/or a tear. Moreover, the analysis may include chemical analysis, genetic analysis (such as genetic sequencing), nuclear quadrapole resonance, nuclear magnetic resonance, and/or electron spin resonance.

Then, the set of biological variables may be optionally converted into categorical data (operation 412), as described previously in the discussion of FIG. 3.

Next, at least some of the biological variables in the set of biological variables may be optionally excluded (operation 414) prior to determining compound variables based on at least some of the biological variables in the set of biological variables (operation 416) (or a remainder of the set of biological variables after the optional excluding in operation 414) and one or more mathematical interactions. For example, a given excluded biological variable may have a number of presence or absences (or, alternatively, expression and/or suppression) in a pattern of occurrence in the set of biological variables (i.e., in the data determined from the biological samples of the group of life forms) which is greater than a first value or less than a second value. This may exclude biological variables that have too few or too many presences or absences for there to be a statistically significant relationship with a pattern of occurrence of the trait associated with the group of life forms. For these excluded biological variables, it may not be possible to determine whether or not there is a relationship with the trait. In an exemplary embodiment, the first value is 5, 10 or 15% presence or absence (respectively) and/or the second value is 85, 90 or 95% absence or presence (respectively).

Additionally, or alternatively, in some embodiments at least some of the determined compound variables may be optionally excluded (operation 418) after determining the compound variables (416). For example, a given excluded compound variable may have a number of presence or absences (or, alternatively, expression and/or suppression) in a pattern of occurrence of the compound variable (i.e., based on the data associated with the group of life forms) which is greater than a third value or less than a fourth value. This may exclude compound variables that have too few or too many presences or absences for there to be a statistically significant relationship with a pattern of occurrence of the trait associated with the group of life forms. For these excluded compound variables, it may not be possible to determine whether or not there is a relationship with the trait. In an exemplary embodiment, the third value is 5, 10, or 15% presence or absence (respectively) and/or the fourth value is 85, 90 or 95% absence or presence (respectively).

As noted above, the compound variables may be determined (416). (Alternatively, the compound variables may be pre-determined, stored in a computer-readable memory, and accessed during process 400.) Moreover, as described further below, this determining or accessing may be iterated in operation 428 (FIG. 4B) at increasingly higher orders, which facilitates the identification of the one or more association variables using hierarchical feature extraction. For example, at first order, a given compound variable may correspond to a pattern of occurrence of a given biological variable.

Then, at second order, a given compound variable may correspond to a pattern of occurrence of one biological variable in the set of biological variables of the group of life forms and a pattern of occurrence of another biological variable in the set of biological variables of the group of life forms. This process may be repeated at ever high order (i.e., with larger groups of biological variables) until the resulting model complexity is sufficient to 'fit' the data or until diminishing returns occur (as described further below).

Note that the given compound variable for an order n may be determined by performing a mathematical operation and/or a logical operation on corresponding entries in the patterns of occurrence of n biological variables. For example, at second order, a particular compound variable may be determined by performing the mathematical operation and/or the logical operation on corresponding entries in a pattern of occurrence of a first biological variable and a pattern of occurrence of the second biological variable (which is described further below with reference to FIG. 5). Note that the mathematical operation may include multiplication. Moreover, the logical operation may include a Boolean operation, such as AND. However, a wide variety of coding approaches may be used in different embodiments for representing presence and/or absence information in the patterns of occurrence of biological variables. Therefore, in some embodiments the logical operation may include AND, OR, NOT, XOR, and/or another Boolean operation.

More generally, for ternary encoded biological variables (such as {0, 1 or 2} for a SNP at a genetic location on two copies of a chromosome across the group of life forms, e.g., a patient population) the mathematical operation used to determine the given compound variable may be one of a set of mathematical operations. For example, the set of mathematical operations may be represented by 3×3 matrices, such as at least some of those provided in Wentian Li et al., "A Complete Enumeration and Classification of Two-Locus Disease Models," Human Heredity vol. 50, pp. 334-349 (2000). (Note that the set of mathematical operations may be selected based on those 3×3 matrices that are expected to provide the largest signal in the identification technique, such as the largest numbers of occurrences in the occurrence ranking.) Thus, the given compound variable may be determined by performing a mathematical operation specified by a given mathematical interaction on corresponding entries in a pattern of occurrence of the first biological variable in the given pair of biological variables and a pattern of occurrence of the second biological variable in the given pair of biological variables.

In some embodiments, one or more compound variables may be a weighted summation of one or more biological variables. For example, for order n, n biological variables may be multiplied by corresponding weights and summed to determine the given compound variable. Moreover, in some embodiments the resulting one or more compound variables may be converted into categorical data using one or more thresholds (thus, converting operation 412 may occur before and/or after the determining operation 416).

Figure 4B:
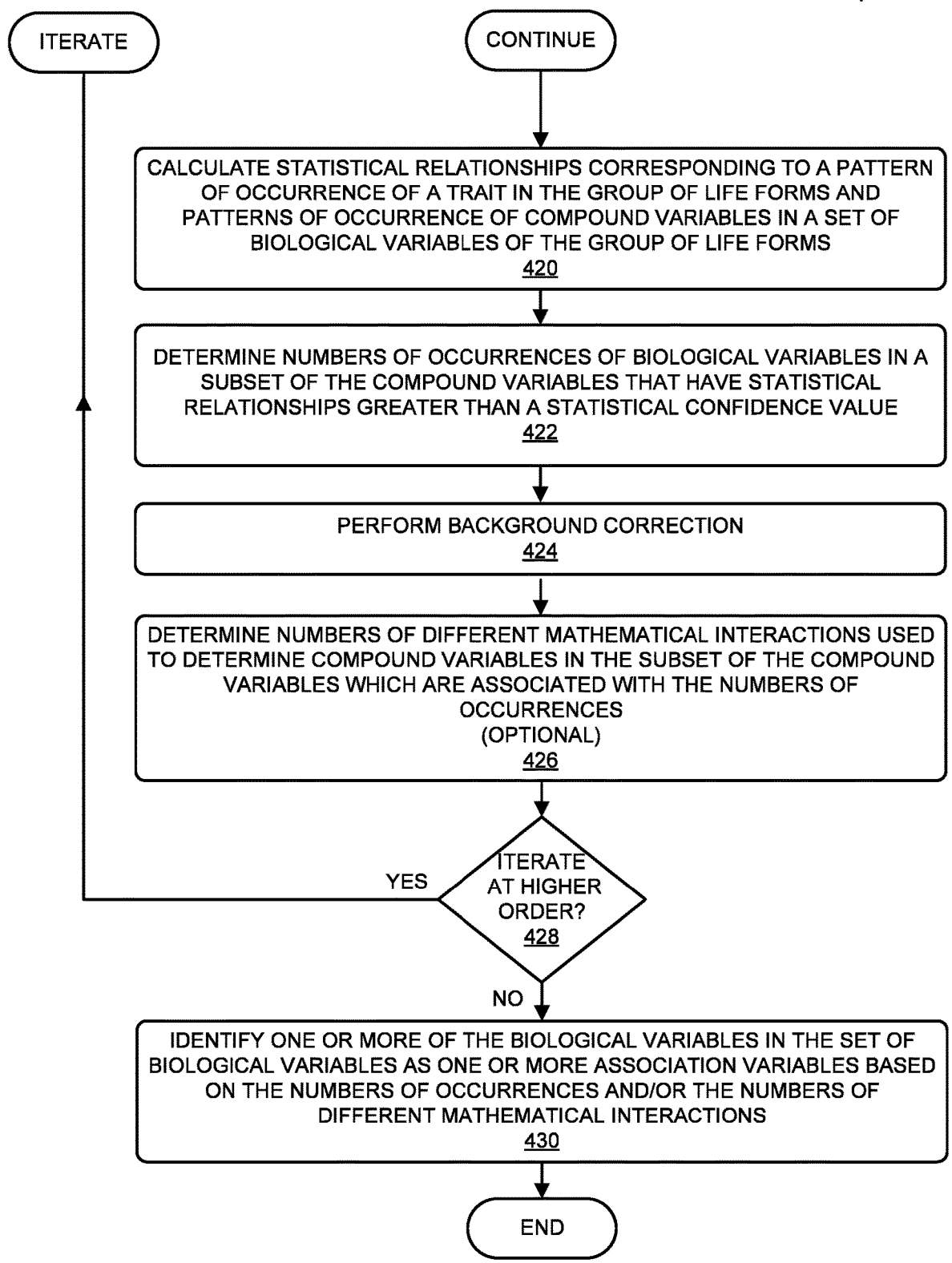
FIG. 4B is a flow chart illustrating a process for identifying one or more association variables that are associated with a trait in accordance with an embodiment of the present disclosure.

Continuing the discussion of process 400 in FIG. 4B, then statistical relationships corresponding to a pattern of occurrence of the trait in a group of life forms and patterns of occurrence of compound variables in a set of biological variables of the group of life forms may be calculated (operation 420). In particular, a given statistical relationship may correspond to the pattern of occurrence of the trait in the group of life forms and the pattern of occurrence of the given compound variable in the set of biological variables of the group of life forms. Note that the calculation may include contributions from presence and/or absence information (or, alternatively, expression and/or suppression information) in the pattern of occurrence of the given compound variable and/or in the patterns of occurrence of the trait.

As described further below, the statistical relationships may be determined using a supervised-learning analysis technique and/or a non-parametric analysis technique, which makes few assumptions about an existence of a probability distribution function (such as a normal distribution) corresponding to the given population from which biological samples and, thus, the data are obtained, or regarding independence of the biological variables and/or the compound variables. In some embodiments, a given statistical relationship may be used to perform hypothesis testing to determine if the associated given compound variable and the trait are statistically independent (or dependent) based on a statistical confidence value (for example, based on a statistical significance value or criterion). In the process, the effective signal-to-noise ratio in an underdetermined problem (e.g., sparse sampling in a multi-dimensional variable space, such as when a number of life forms in the group of life forms is significantly less than a number of biological variables in the set of biological variables) may be improved by restricting a number of local fitting neighborhoods (e.g., a number of relevant biological variables and/or compound variables), thereby reducing the requirements associated with the Bonferroni correction.

Note that in some embodiments 'significantly less than' includes a multiplicative factor of 2, 5, 10, 100, 1000, $10^4$, $10^5$, $10^6$, $10^7$, or more. Thus, the number of life forms in the group of life forms may be at least 1000 times less than the number of biological variables in the set of biological variables. In an exemplary embodiment, the number of life forms is 3700 and the number of biological variables in the set of biological variables is 500,000.

Next, numbers of occurrences of biological variables that were used to determine the compound variables in a subset of the compound variables that have statistical relationships greater than a statistical confidence value may be determined (422). For example, an occurrence ranking based on the numbers of occurrences may be determined. (This is described further below with reference to FIGS. 6 and 7A.)

Moreover, a background correction may be performed (operation 424). For example, the additional statistical relationships may be calculated (as in operation 420) using a sequence of values (such as a random or a pseudorandom sequence having the same number of entries as the number of life forms in the group of life forms) instead of the pattern of occurrence of the trait. Then, another occurrence ranking for another subset of these additional statistical relationships that are significant may be determined (as in operation 422) and may be subtracted from the occurrence ranking. Note that significance of the other subset of the additional statistical relationships may be determined using another statistical confidence value, which may be different that the statistical confidence value.

Additionally, numbers of different mathematical interactions used to determine the compound variables in the subset of the compound variables for the biological variables that are associated with the corresponding numbers of occurrences may be optionally determined (operation 426). For example, an interaction ranking of the biological variables in the subset may be determined based on the numbers of different mathematical interactions associated with these biological variables. (This is described further below with reference to FIG. 7B.)

As noted previously, operations 416-426 may be iterated (operation 428) using progressively higher-order compound variables to determine the statistical relationships and the rankings. In some embodiments, at least a portion of the occurrence ranking for the current order is used to determine the compound variables (416) (FIG. 4A) at the next higher order. As described further below, these iterations may be continued until a model that describes the relationship between the patterns of occurrence of the compound variables in the set of biological variables and the pattern of occurrence of the trait is obtained or diminishing returns occur (such as an increase in an error associated with predictions of the model based on training data and test data).

Next, one or more of the biological variables in the set of biological variables may be identified (operation 430) as the one or more association variables based on the numbers of occurrences (e.g., the occurrence ranking) and/or the numbers of different mathematical interactions (e.g., the interaction ranking). As described further below with reference to FIG. 7A, the one or more association variables may be identified in occurrence rankings that are above a noise floor in the statistically significant compound variables. For example, at least a subset of such occurrence rankings may be approximately stable, and the biological variables in such subsets may be the one or more association variables. As is also described further below, note that the one or more association variables may have a relationship or an anti-relationship with the occurrence of the trait in the given population.

In some embodiments, process 400 includes additional or fewer operations. Moreover, the order of the operations may be changed and/or two or more operations may be combined into a single operation. For example, in some embodiments compound variables may be determined (416) (FIG. 4A) using biological variables associated with time intervals (which may be the same as each other, may be different than each other, and/or may be offset from each other) that precede a change in the trait in individual life forms in the group of life forms (such as the occurrence of cancer, an increase of a symptom, and/or an onset of an episode of an episodic disease). In some embodiments, the time intervals include: minutes, hours, days, months, and/or years. In an exemplary embodiment for migraines, at second order, a particular compound variable corresponds to a pattern of occurrence of a first biological variable in a first time interval preceding one or more migraines (such as one day before each migraine in a sequence of migraines) and a pattern of occurrence of a second biological variable in a second time interval preceding the one or more migraines (such as between one and two days before each migraine in the sequence of migraines).

In some embodiments, at least some of the operations in process 400 (FIGS. 4A and 4B) are repeated to identify subgroups or subpopulations in the given population or group of life forms. For example, one or more subgroups may be determined based on the one or more identified association variables for different portions of the group of life forms. Note that the one or more subgroups may be indicative of underlying polymorphism in a genetic basis for a given trait.

Figure 5:
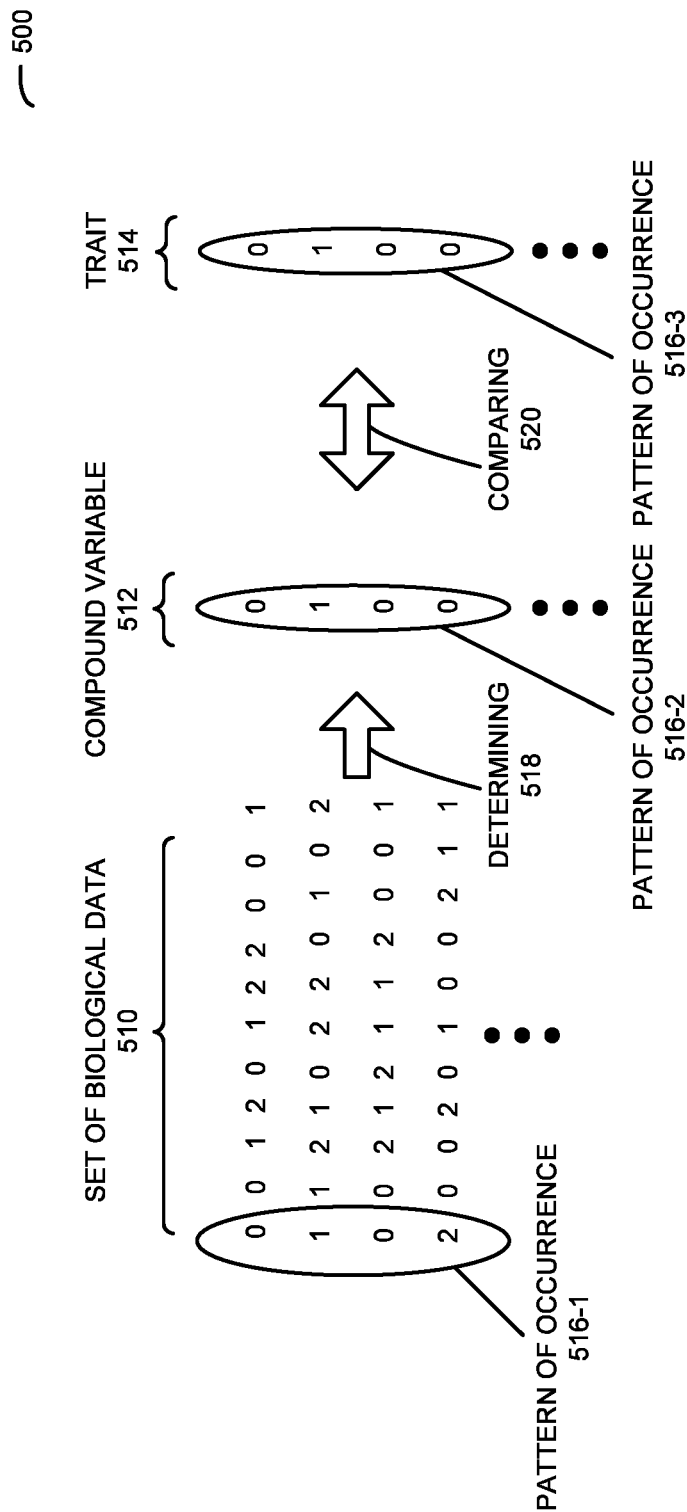
FIG. 5 is a drawing illustrating identifying one or more association variables that are associated with a trait in accordance with an embodiment of the present disclosure.

We now describe examples of operations in process 400 (FIGS. 4A and 4B). FIG. 5 presents a drawing 500 illustrating identifying one or more association variables that are associated with a trait. Set of biological variables 510 may include multiple biological variables (the columns) associated with multiple life forms in a group of life forms (the rows). In general, the presence or absence (or, expression and/or suppression) of a given biological variable varies in the data and, thus, across or over the group of life forms. (For example, for a given life form, presence of the given biological variable at a given genetic location on both copies of a chromosome may be indicated by a '2', presence of the given biological variable at the given genetic location on one copy of a chromosome may be indicated by a '1', and absence of the given biological variable at the given genetic location may be indicated by a '0'.) This variation defines the patterns of occurrence of each of the biological variables, such as pattern of occurrence 516-1.

Similarly, information for the occurrence of trait 514 may vary across or over the group of life forms (the rows in trait 514). For example, trait 514 may be present in one life form (as indicated by a '1') and absent in another (as indicated by a '0'). (Alternatively, '0's and '1's may indicate suppression and expression, respectively, of trait 514.) This variation defines the patterns of occurrence 516-3 of trait 514.

Moreover, one or more biological variables in the set of biological variables 510 may be used to determine 518 compound variable 512. For example, at second order, entries in two of the set of biological variables 510 may be combined according to a particular mathematical operation, such as the M21 penetrance table in Wentian Li et al., "A Complete Enumeration and Classification of Two-Locus Disease Models," Human Heredity vol. 50, pp. 334-349 (2000). In this case, if an entry in a first biological variable is a '0' and an entry in a second biological variable is a '1', this specifies row 0, column 1 in the M21 penetrance table, which results in a row entry of a '0' in compound variable 512. In general, the resulting entries in compound variable 512 may vary across or over the group of life forms (the rows in compound variable 512). This variation defines the patterns of occurrence 516-2 of compound variable 512.

Then, patterns of occurrence 516-2 and 516-3 may be used to calculate a statistical relationship for each life form in the group of life forms (i.e., using the entries in compound variable 512 and trait 514 on a row by row basis). For example, the statistical relationship may be determined by comparing 520 entries in compound variable 512 and trait 514 using a statistical analysis technique. This process may be repeated for multiple combinations of the biological variables in the set of biological variables 510 (i.e., multiple compound variables based on the same or different mathematical operations in the set of mathematical operations) to generate a set of statistical relationships with trait 514 for a given order in the analysis.

Figure 6:
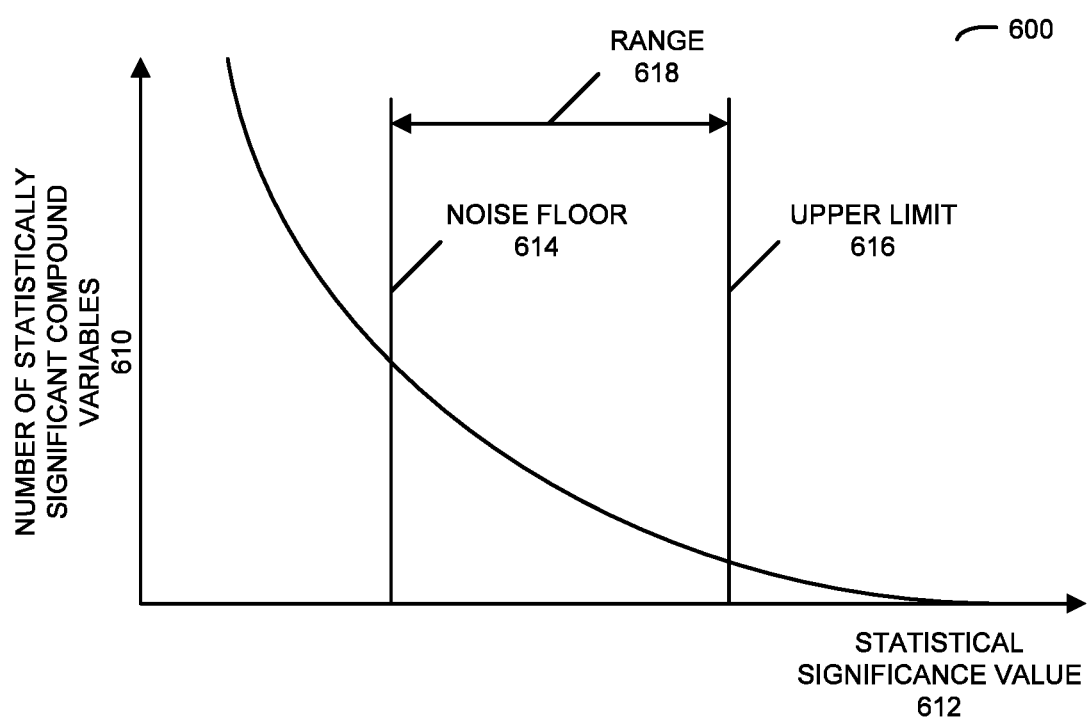
FIG. 6 is a graph of a number of statistically significant compound vectors as a function of statistical significance value in accordance with an embodiment of the present disclosure.

Next, the set of statistical relationships may be compared to statistical confidence values (such as a statistical significance value or criterion) to identify a noise floor in the set of statistical relationships. This is shown in FIG. 6, which presents a graph 600 of a number of statistically significant compound vectors 610 (i.e., compound vectors having statistical relationships with the trait that exceed a statistical significance value) as a function of statistical significance value 612. As the statistical significance value 612 is increased, the number of statistically significant compound vectors 610 decreases. If the signal-to-noise ratio in the set of biological variables 510 (FIG. 5) and the trait 514 (FIG. 5) is sufficiently large (for a given size of or number of members in the group of life forms) then at least a portion of occurrence rankings of the numbers of occurrences of biological variables in the statistically significant compound vectors 610 between a minimum value of the statistical significance value 612 and an upper value 616 of the statistical significance value 612 is substantially or approximately stable. (One metric for whether or not the signal-to-noise ratio is sufficiently large may be that the expectation value for the number of statistically significant compound variables for a given statistical significance value is less than the actual number of statistically significant compound vectors at the given statistical significance value.) This minimum value may be noise floor 614. Note the upper value 616 occurs because, eventually, as the statistical significance value 612 is increased, the number of statistically significant compound vectors 610 decreases to the point where the remaining statistically significant compound vectors 610, and thus the corresponding occurrence rankings, are dominated by statistical outliers. Consequently, for a large enough statistical significance value 612, the occurrence ranking may no longer be substantially or approximately stable.

Figure 7A:
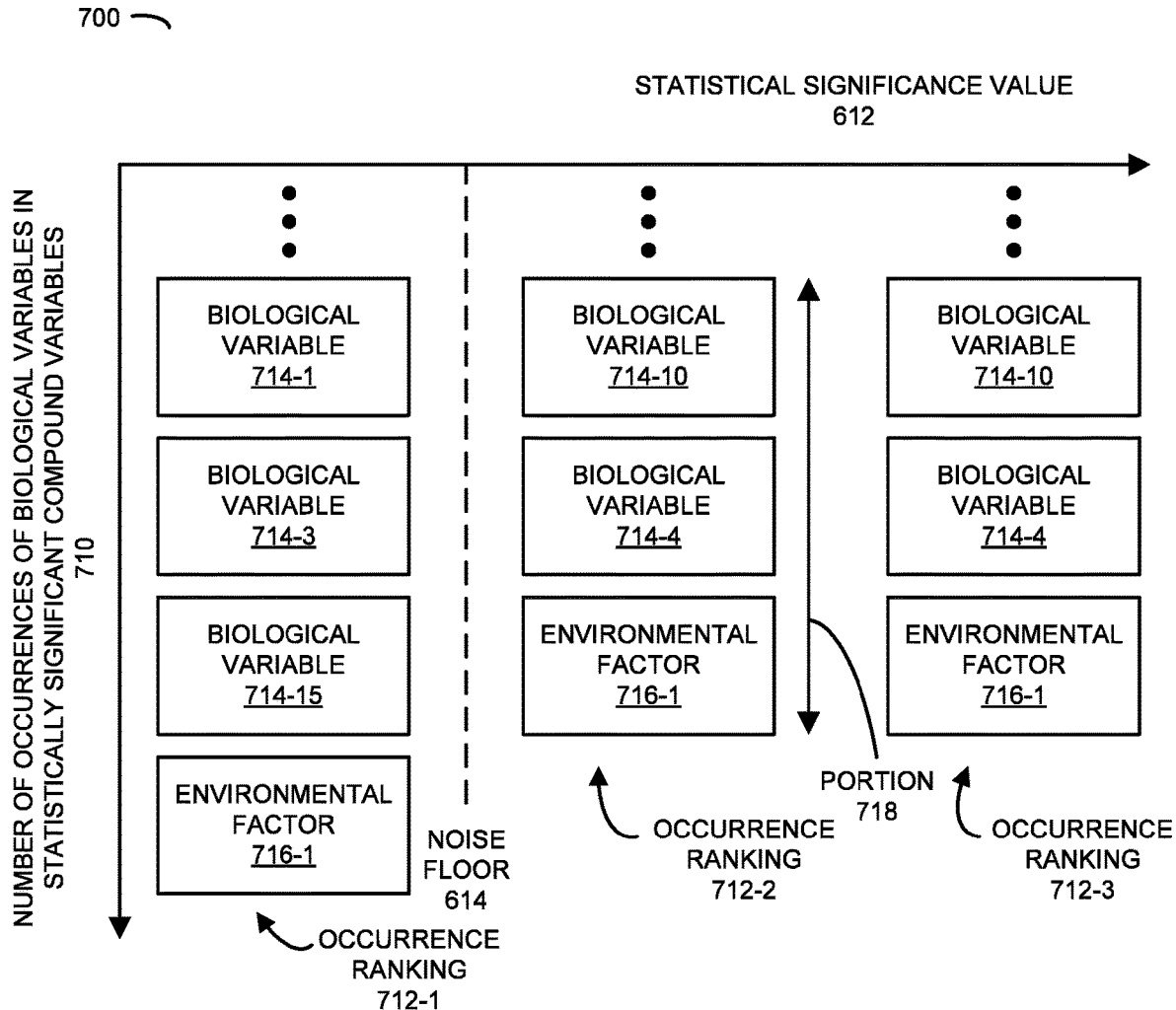
FIG. 7A is a drawing of an occurrence ranking of numbers of occurrences of biological variables in statistically significant relationships as a function of statistical significance value in accordance with an embodiment of the present disclosure.

FIG. 7A presents a drawing 700 of an occurrence ranking of numbers of occurrences of biological variables in statistically significant compound variables 710 as a function of statistical significance value 612. As the statistical significance value 612 increases, at least a portion 718 of occurrence rankings, such as occurrence rankings 712-2 and 712-3, above the noise floor 614 is substantially or approximately stable. (In contrast, occurrence ranking 712-1 may not be stable, i.e., when the statistical significance value 612 increases, occurrence ranking 712-1 may change.) For example, a given occurrence ranking, such as occurrence ranking 712-2, may be considered to be substantially or approximately stable if 50%, 70%, 75%, 80%, 85%, 90%, 95% or 100% of the top-N biological variables (such as the top-20) in the given occurrence ranking are unchanged when the statistical significance value 612 is increased.

Note that portion 718 may include one or more biological variables, such as environmental factor 716-1 and/or one or more of biological variables 714. Moreover, at least portion 718 in occurrence rankings 712-2 and 712-2 may indicate or specify a pareto. Furthermore, the one or more association variables may be identified in portion 718 or in occurrence rankings 712-2 and 712-3 that are substantially or approximately stable.

Figure 7B:
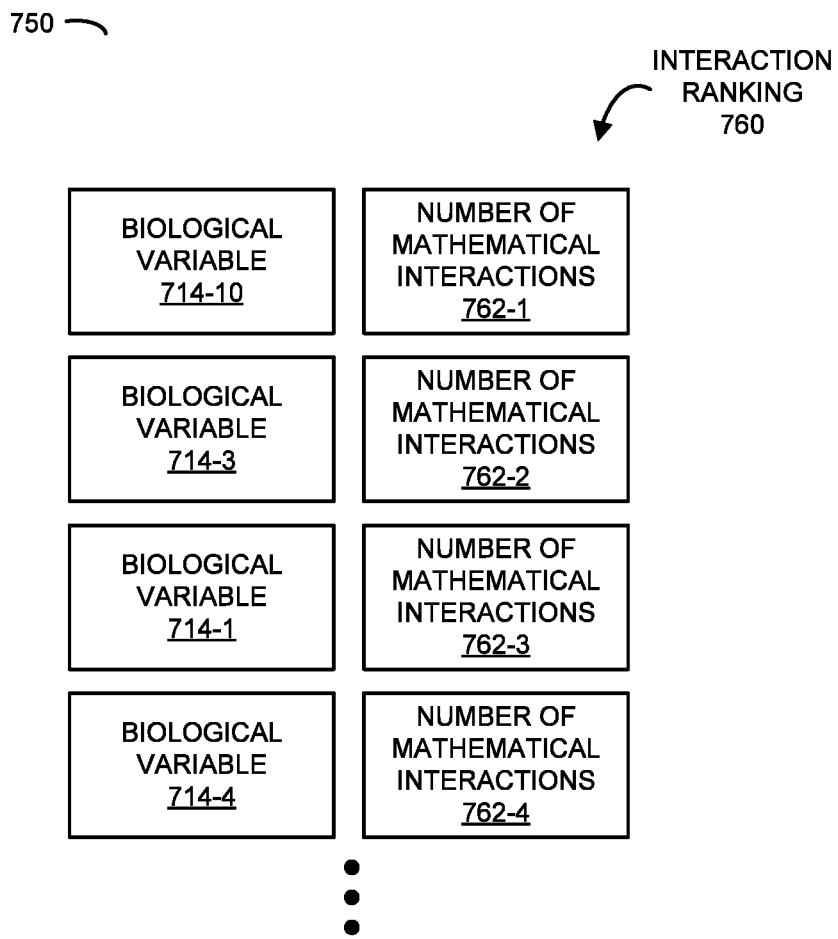
FIG. 7B is a drawing of an interaction ranking of numbers of different mathematical interactions used to determined compound variables in a statistically significant subset of the compound variables that are associated with the corresponding numbers of occurrences in accordance with an embodiment of the present disclosure.

Once a substantially or approximately stable occurrence ranking is determined, it can be used to determine an interaction ranking. This is shown in FIG. 7B, which presents a drawing 750 of an interaction ranking 760 of numbers of different mathematical interactions used to determined compound variables in a statistically significant subset of the compound variables that are associated with the corresponding numbers of occurrences. In particular, interaction ranking 760 may provide a pareto of biological variables 714 based on a number of different mathematical interactions 762 with which they are used to determine compound variables in the statistically significant subset of the compound variables. In this example, biological variable 714-10 is at the top of interaction ranking 760. Biological variable 714-10 may occur 500 times in the tens of thousands of statistically significant compound variables, and 20 different mathematical interactions may have been used, in conjunction with biological variable 714-10, to determine these 500 compound variables. Similarly, biological variable 714-3 is second in interaction ranking 760. Biological variable 714-3 may occur 100 times in the tens of thousands of statistically significant compound variables, and 14 different mathematical interactions may have been used, in conjunction with biological variable 714-3, to determine these 100 compound variables.

Note that the assumption that underlies occurrence rankings 712 (FIG. 7A) and interaction ranking 760 is that the biological variables interact with each other according to a graph with nodes and branches. While the underlying interactions are assumed to be biological in nature, in the present analysis the interactions are studied and identified based on mathematical interactions (which may or may not reflect the underlying biological interactions). In this graph, nodes that are more important are those that have more branches. Thus, by considering the number of occurrences of a given node in the subset, the relative importance of the given node relative to other nodes in the graph can be assessed using an occurrence ranking.

Similarly, the mathematical interactions provide very selective filtering as the biological variables are combined to determine compound variables. As the order n is increased, it is increasingly difficult to find a pattern of occurrence of a given biological variable for a given mathematical interaction that, in conjunction with a compound variable of order n−1, improves the statistical association with the pattern of occurrence of the trait. (In fact, using the given mathematical interaction the pattern of occurrence of the given biological variable typically results in a weaker statistical association.) In general, if a first mathematical interaction for a pair of biological variables results in a statistically significant association, a different mathematical interaction is needed to determine a statistically significant association between a third biological variable and either of the biological variables in the pair of biological variables. Thus, assuming that the graph includes sequences of multiple interacting nodes (i.e., biological variables), these can be identified by looking for biological variables that are associated with multiple different mathematical interactions in an interaction ranking.

In an exemplary embodiment, the identification technique was used to identify association variables for major depressive disorder using the GAIN SNP dataset (available via dbGaP) for 3741 individuals (about 50% of whom had major depressive disorder). After correcting for linkage disequilibrium and excluding data for the Y chromosome, there were approximately 240,000 SNP variables (which were the biological variables in this example). Using 28 mathematical interactions specified in Wentian Li et al., "A Complete Enumeration and Classification of Two-Locus Disease Models," Human Heredity vol. 50, pp. 334-349 (2000), approximately a half a trillion compound variables were determined at second order (i.e., pairs of biological variables). (In particular, the penetrance tables used were: M1, M3, M7, M10, M11, M13, M14, M17, M21, M26, M27, M30, M41, M42, M45, M58, M69, M78, M85, M86, M97, M99, M101, M106, M113, M114, M170, and M186.) The noise floor in the occurrence rankings occurred for a log-likelihood ratio of 9. As a consequence, occurrence rankings were determined for log-likelihood ratios between 9 and 24. After subtracting the background associated with a pseudorandom sequence of values, the association variables were identified from the occurrence ranking using the interaction ranking.

These association variables are summarized in Table 1, including: the SNP identifier, the occurrence ranking position, the interaction ranking position and, if appropriate, the gene name and gene identifier. Note that 70-80% of the genetic locations specified by these association variables are within or proximate to (within 10,000 base pairs) of genes (far larger than would be expected for random results). The top association variables in Table 1 include known genes that have been determined to be associated with major depressive disorder (such as the glutamate receptor GRM7) and new genes that have not been previously reported. These new genes appear to be associated with low-level synaptic signaling, which seems plausible based on a biological model of the disease. Moreover, the genetic loci that do not include genes may not be false positives. Instead, these locations may play another role, for example, they may be regulators. Furthermore, p-values for the results in Table 1 are estimated to be smaller than $10^{-10}$.

The results in Table 1 are considered surprising because prior analyses of this dataset using existing techniques were unsuccessful. Indeed, the expectation value for false-positive but statistically significant compound variables (for example, for log-likelihood ratios larger than 25 or 30) is 2-4× larger than the number of statistically significant compound variables that were determined using the identification technique (i.e., the results in Table 1 were obtained even though the dataset is theoretically too small for existing analysis techniques to obtain meaningful results). Furthermore, the results in Table 1 were obtained via the identification technique using no adjustable parameters (i.e., the analysis has not been optimized for this dataset or at all).

TABLE 1

| SNP Identifier | Occurrence Ranking Position | Interaction Ranking Position | Gene Name | Gene Identifier |
| --- | --- | --- | --- | --- |
| ss68857569 | 1 | 2 | RBMS3 RNA binding motif | 27303 |
| ss68851703 | 2 | 3 | GRM7 glutamate receptor | 2917 |
| ss69175684 | 2 | 9 | SHC4 SHC | 399694 |
| ss68792332 | 3 | 6 | Miscellaneous RNA | 100505832 |
| ss68785435 | 4 | 6 | FAM5B | 57795 |
| ss68900302 | 5 | 7 | None | None |
| ss68807991 | 6 | 5 | ALK anaplastic lymphoma receptor tyrosine kinase | 238 |
| ss68763914 | 7 | 1 | None | None |
| ss68832152 | 7 | 4 | GALNT13 | 114805 |
| ss68878261 | 7 | 5 | None | None |
| ss68875798 | 7 | 8 | None | None |
| ss68878765 | 8 | 3 | CP ceruloplasmin | 1356 |
| ss68778518 | 8 | 4 | None | None |
| ss68767116 | 8 | 9 | DAB1 | 1600 |
| ss68766841 | 9 | 5 | C8A and C8B | 731, 732 |
| ss68863700 | 9 | 6 | CADPS | 8618 |
| ss68888448 | 9 | 6 | RGS12 | 6002 |
| ss68785445 | 9 | 8 | FAM5B | 57795 |
| ss69020583 | 9 | 8 | PCLO piccolo | 27445 |

Collectively, these results suggest that the interaction technique has information gain relative to existing analysis techniques, and that it can be applied to an arbitrary dataset. This indicates that the interaction technique may be able to identify association variables even for extremely underdetermined problems, such as those associated with full genome sequencing.

We now further describe embodiments of the statistical analysis. This statistical analysis may include classification and/or regression (such as determining a model of the one or more traits, which includes one or more biological variables and/or one or more compound variables, along with corresponding weights).

A wide variety of computational techniques may be used to determine the one or more statistical relationships, including: one or more parametric analysis techniques, one or more non-parametric analysis techniques, one or more supervised learning techniques and/or one or more unsupervised learning techniques. In some embodiments, one or more non-parametric analysis techniques may be used. As noted previously, non-parametric analysis techniques make few assumptions about an existence of a probability distribution function, such as a normal distribution, corresponding to the given population (or group of life forms) from which samples or associated data are obtained, or regarding independence of the biological variables and/or the compound variables. In general, non-parametric analysis techniques may use rank or naturally occurring frequency information in the data to draw conclusions about the differences between different populations or subsets of the given population.

Note that the one or more non-parametric analysis techniques may perform hypothesis testing, e.g., to test a statistical significance of a hypothesis. In particular, the one or more non-parametric analysis techniques may determine if the one or more traits and/or the one or more compound variables are statistically independent (or dependent) based on a statistical significance value or criterion. As noted previously, one or more compound variables having a statistically significant relationship with the trait (and, in particular, the pattern of occurrence of the trait for the group of life forms) may be used to identify the one or more association variables.

In exemplary embodiments, the non-parametric analysis technique may include: a chi-square analysis technique, a log-likelihood ratio analysis technique (also referred to as G-test), and/or a Fisher's exact probability analysis technique. In addition to their other advantages, these techniques may be well suited to analyzing an underdetermined problem, i.e., sparse sampling in a multi-dimensional variable space, in which there may be multiple biological variables and/or compound variables and a smaller number of members of the group of life forms (and, thus, a smaller number of entries in these variables and in the trait information).

In some embodiments, the chi-square analysis technique, the log-likelihood ratio analysis technique, and/or the Fisher's exact probability analysis technique may be determined using a cross-tabulation or contingency tables (which are sometimes referred to as bivariate tables). Note that the Fisher's exact probability analysis technique computes the sum of conditional probabilities of obtaining the observed frequencies in a given contingency table and the conditional probabilities of obtaining exactly the same observed frequencies for any configuration that is more extreme, i.e., having a smaller conditional probability. Moreover, the chi-square ($\chi^2$) may be determined using $$\chi^2 = \sum_i \frac{(O_i - E_i)^2}{E_i},$$

and the log-likelihood ratio (LLR) using $$LLR = \sum_i O_i \ln\left(\frac{O_i}{E_i}\right),$$

where the summation is over the entries in the given contingency table, $O_i$ is the i-th observed frequency value, and $E_i$ is the i-th expected frequency value. The following example illustrates an exemplary embodiment of determining a statistical relationship using the log-likelihood ratio for binary categorical data.

Consider the example contingency table in Table 2. The first column contains the number of entries in the pattern of occurrence where a compound variable is present and the trait is present (which is henceforth denoted by $X_{11}$) in the data (such as genetic data) associated with the group of life forms plus the number of entries in the pattern or occurrence where the compound variable is absent and the trait is absent in the data associated with the group of life forms (which is henceforth denoted by $X_{00}$). $X_{11}$ is sometimes referred to as a true-true and $X_{00}$ is sometimes referred to as a false-false. $X_{11}$ and $X_{00}$ are henceforth referred to as co-occurrences.

The second column in Table 2 contains the number of entries in the pattern of occurrence where the compound variable is present and the trait is absent (henceforth denoted by $X_{10}$) in the data associated with the group of life forms plus the number of entries in the pattern of occurrence where the compound variable is absent and the trait is present (henceforth denoted by $X_{01}$) in the data associated with the group of life forms. $X_{10}$ is sometimes referred to as a true-false and $X_{01}$ is sometimes referred to as a false-true. $X_{10}$ and $X_{01}$ are henceforth referred to as cross occurrences.

TABLE 2

| Number of Co-Occurrences ($X_{11} + X_{00}$) | Number of Cross Occurrences ($X_{10} + X_{01}$) |
|---|---|
| 46 | 11 |

If the compound variable and the trait are completely independent, the expected frequency values for each column, $E_1$ and $E_2$, would equal 28.5, one half of the sum of the number of co-occurrences and cross occurrences, i.e., the total number of observations (data points or samples) in Table 2. Therefore, for Table 2, $$LLR = 2 \cdot 46 \ln\left(\frac{46}{28.5}\right) + 2 \cdot 11 \ln\left(\frac{11}{28.5}\right) = 44.04 - 20.94 = 23.10.$$

A one-sided minimal statistical significance confidence value or criterion of 5% ($\alpha=0.05$) or a statistical confidence threshold based on the number of degrees of freedom (the size of the contingency table, which in this example is one) corresponds to an LLR of 3.841. (Note that if the biological variables have more than two categories, the contingency table may have a larger number of degrees of freedom.) Because the LLR for Table 2 is greater than 3.841, it is statistically significant. Therefore, from a statistical perspective, the null hypothesis is rejected and the patterns of occurrence of the compound variable and the trait in the data associated with the group of life forms in this example are dependent.

Note that it is possible for statistically significant LLR values to occur even when $X_{11}$ is zero. In some embodiments, compound variables that have $X_{11}$ equal to zero when compared with the pattern of occurrence of the trait are excluded prior to determining the rankings and identifying the one or more association variables. Additionally, note that the LRR value is the same when there is a relationship (when the number of co-occurrences is greater than the number of cross occurrences) or an anti-relationship (when the number of co-occurrences is less than the number of cross occurrences) between the pattern of occurrence of the compound variable and the pattern of occurrence of the trait. Consequently, in embodiments where association variables corresponding to relationships are desired, statistical relationships where the number of co-occurrences is less than the number of cross occurrences may be excluded. Similarly, in embodiments where association variables corresponding to anti-relationships are desired, statistical relationships where the number of co-occurrences is greater than the number of cross occurrences may be excluded. Furthermore, in some embodiments, instead of using an occurrence ranking corresponding to the sequence of values to perform the background correction, an occurrence ranking of the number of occurrences of biological variables in statistical relationships corresponding to no relationship (i.e., an LLR of infinity, or when the number of co-occurrences equals the number of cross occurrences) may be used.

In the preceding example, the calculation of the statistical relationship for the trait and the compound variable uses presence and absence information in the patterns of occurrence of the compound variable and the trait. In some embodiments, one or more of the statistical relationships may be determined using presence information, i.e., the presence only (or absence only) of one or more compound variables in the data associated with the group of life forms, without using absence information (or without using presence information). In alternate embodiments, a wide variety of analysis techniques may be used to calculate the one or more statistical relationships.

In parametric analysis, a Pearson's product-moment correlation coefficient r may be useful in summarizing a statistical relationship. For some contingency tables, Cramer's phi q, the square root of $\chi^2$ or the LLR divided by the number of observations N, may have a similar interpretation to r (although, it is known that Cramer's phi φ may underestimate r). In the example illustrated in Table 2, $$\varphi = \sqrt{\frac{LLR}{N}} = \sqrt{\frac{23.1}{57}} = 0.64.$$

The chi-square analysis technique and the log-likelihood ratio analysis technique may have a maximal sensitivity for contingency tables based on patterns of occurrence of compound variables having 50% presence entries and 50% absence entries in the data associated with the group of life forms. In addition, maximal sensitivity may occur if 50% of the life forms in the group of life forms have the trait, e.g., presence entries. In some embodiments, one or more contingency tables may be generated to achieve approximately 50% presence entries for patterns of occurrence of one or more compound variables and/or 50% having the trait by using a subset of the data associated with the group of life forms. In an exemplary embodiment, one or more contingency tables may be generated by randomly or pseudo-randomly selecting (for example, using a pseudo-random number generator or technique) a subset of the data associated with the group of life forms, such that the one or more contingency tables may have approximately 50% presence entries and 50% absence entries distributed over $X_{00}$, $X_{11}$, $X_{10}$, and $X_{01}$. For infrequently occurring events, biological variables and/or compound variables, there may be more absence entries than presence entries in the data associated with the group of life forms. As a consequence, different sampling ratios may be used for presence and absence entries in the data associated with the group of life forms.

In some embodiments, boosting may be used when generating one or more contingency tables. A subset of the data associated with group of life forms may be selected randomly or pseudo-randomly in order to determine one or more contingency tables. A given contingency table may be generated L times using approximate random sampling. Statistical relationships for at least M of these L contingency tables may be used (including combining and/or averaging) to determine whether or not the trait and the corresponding compound variable are independent in the data associated with the group of life forms. In an exemplary embodiment, L may be 5, 10, 25, 50, 100, 500 or more, and M may be 50% (rounded to the nearest integer), 60%, 66%, 70%, 75%, 80% or more of L.

In some embodiments, there may be too few presence entries or too many presence entries in one or more patterns of occurrence of one or more biological variables or compound variables in the data associated with the group of life forms to reliably determine statistically significant independence (or dependence) based on the trait information for the group of life forms, i.e., the pattern of occurrence of the trait in data associated with the group of life forms. As a consequence, one or more of these biological variables or one or more of these compound variables may be excluded when determining one or more statistical relationships. In an exemplary embodiment, one or more biological variables or one or more compound variables having patterns of occurrence with less than 15% presence entries or more than 85% presence entries in the data associated with the group of life forms may be excluded.

Overfitting or developing a model that is too complex is a risk in a statistical learning problem. In some embodiments, the model complexity may correspond to a number of compound variables that have statistically significant dependence on the trait information. Moreover, in some embodiments the model complexity may, at least in part, correspond to a number of biological variables included when determining a given compound variable, i.e., the order n.

In some embodiments, this risk may be addressed using a fraction or percentage of the data associated with the group of life forms (such as the patterns of occurrence) for training, i.e., to develop the model, and a remainder for testing the resulting model. Typically training error decreases as the model complexity increases (the model better fits or predicts a training set of data), and a testing error exhibits a minimum. Additional model complexity beyond this minimum usually does not generalize well (the model offers a poorer fit or prediction for a test set of data). Therefore, beyond the minimum point the training set of data may be overfit. In an exemplary embodiment, the percentage of the data associated with the group of life forms used for training may be 70%, 75%, 80%, 85% or 90%.

An additional metric of the model complexity may be determined. This metric may be used in conjunction with or independently of the training set of data and the test set of data. The additional metric is described below. In some problems and/or embodiments, calculating one or more statistical relationships for one or more biological variables (or, said differently, for one or more compound variables of order 1) may not be sufficient to determine statistically significant independence (or dependence) with respect to trait information. For example, in multi-dimensional problems, where two or more biological variables are necessary and sufficient to give rise to a trait (such as migraine), a value of the Fisher's exact probability, $\chi^2$, and/or LLR for a compound variable of order 1 may be reduced since there is a penalty for the presence of the cross occurrences, $X_{10}$ and $X_{01}$.

More generally, the value of the Fisher's exact probability, $\chi^2$, and/or LLR may be reduced if the order n of one or more compound variables is less than an intrinsic order of the multi-dimensional problem. In the case of $X_{10}$, a trait may or may not occur unless a certain number of biological variables or a set of biological variables (which may be inter-operative) are present for particular life forms in the group of life forms. And in the case of $X_{01}$, more than one set of biological variables may be present, i.e., one or more biological variables in another set of biological variables may lead to the trait in the particular life forms. (Moreover, for environmental factors, there may be one or more thresholds, which may be a function of time.)

To assess whether or not the model has sufficient complexity, i.e., whether or not one or more compound variables have been determined to sufficient order n, a ratio R may be determined. For contingency Table 2, R is defined as $X_{11}$ divided by the total number of occurrences of the compound variable of order n in the data associated with the group of life forms, i.e., $$R = \frac{X_{11}}{(X_{11} + X_{10})}.$$

An increasing value of R, and/or Cramer's phi $\varphi$, as statistical analysis is performed to higher order (i.e., n+1) may be metrics of goodness, i.e., it may indicate that the higher order does a better job determining statistically significant independence or dependence between one or more compound variables and the trait information. In some embodiments, contingency tables for one or more compound variables may be generated for progressively higher orders (e.g., by iterating at least some of the operations in process 400 in FIGS. 4A and 4B). Once the ratio R is close to or equal to one, i.e., $X_{10}$ is close to or equal to zero, further increases in the order n of one or more compound variables may not be needed (the model has sufficient complexity). Note that in some embodiments, statistical entropy may be used to determine if further increases in the order n of one or more compound variables are needed.

One or more variables and/or compound variables having statistically significant statistical relationships with the trait information for the group of life forms may be identified as one or more association variables. For a given compound variable of order n having a significant statistical relationship with the trait information, the n constituent biological variables may be identified as n association variables and/or as a set of association variables. In some embodiments, one or more statistically significant compound variables of order n having the ratio R approximately equal to 1 may be identified as one or more association variables.

In some embodiments, one or more compound variables of order n and/or one or more constituent biological variables in the one or more compound variables of order n may be ranked based on the corresponding calculated statistical relationships that are statistically significant. In some embodiments, an occurrence ranking of a given constituent biological variable is based on a number of occurrences of the given constituent biological variable in one or more compound variables of order n having statistical relationships that are statistically significant. As noted previously, occurrence rankings may be performed as the statistical significance confidence value or criterion ($\alpha$) is progressively increased, which can be used to determine the noise floor in the statistical relationships (as described previously in the discussion of FIG. 6, and as described further below). Additionally, once a suitable statistical significance confidence value or criterion is found (based on substantial or approximate stability of the occurrence rankings), an interaction ranking may be determined based on the numbers of different mathematical interactions used to determine the compound variables in the subset of the compound variables for the biological variables that are associated with the corresponding numbers of occurrences.

In exemplary embodiments, $\alpha$ may be 0.05 or lower. For a given occurrence ranking, a pareto corresponding to at least a portion of the given occurrence ranking may be defined. This pareto may correspond to biological variables or compound variables having a statistical relationship or a number of occurrences in the statistically significant compound variables exceeding a threshold. In some embodiments, a top-10, 20, 50 or 100 biological variables or compound variables may be used, or a majority of the top-10, 20, 50 or 100 biological variables or compound variables may be used. For compound variables of order n, approximate stability of the pareto as the statistical significance value or criterion is increased may be used to identify the noise floor. Approximately stability may include an approximately unchanged order of the ranking or a presence of approximately the same biological variables and/or compound variables (for example, more than 70 or 80%) in the portion of the occurrence ranking. In exemplary embodiments, the noise floor may correspond to an $\alpha$ of 0.01 or lower, an $\alpha$ of 0.001 or lower, or an $\alpha$ of 0.0001 or lower.

Additionally, once a suitable statistical significance confidence value or criterion is found (based on substantial or approximate stability of the occurrence rankings), an interaction ranking may be determined based on the numbers of different mathematical interactions used to determine the compound variables in the subset of the compound variables for the biological variables that are associated with the corresponding numbers of occurrences. One or more biological variables and/or one or more compound variables in paretos corresponding to one or more statistical significance values or criteria that exceed the noise floor and which may be associated with the largest numbers of different mathematical interactions may be identified as association variables.

In some embodiments, the analysis is repeated using a random or pseudo-random sequence of values instead of the trait information. This sequence of values may have the same length (or number of entries) as the number of life forms in the group of life forms. Moreover, the resulting occurrence ranking, which may be determined using the same or a different statistical significance value or criterion as the occurrence ranking described above, may be subtracted from the occurrence ranking described above before the one or more association variables are identified.

In some embodiments, one or more biological variables and/or one or more compound variables in paretos corresponding to one or more statistical significance values or criteria that exceed the noise floor may be used as a seed set in additional statistical analysis. The additional statistical analysis may determine statistical relationships for compound variables of a higher order. In some embodiments, the additional analysis may utilize an analysis technique such as SVM or CART.

Alternatively, the additional analysis technique may be used as the initial or first stage, to refine the model (including adding or removing one or more biological variables and/or one or more compound variables), and/or to identify one or more association variables.

Note that the additional analysis technique may include classification and/or regression (such as determining a model of the trait information including one or more biological variables and/or one or more compound variables, along with corresponding weights). As with the statistical analysis technique described previously, a wide variety of techniques may be used in the additional analysis technique. Two such techniques, SVM and CART, are described further below. In some embodiments, separately or in conjunction with the additional statistical analysis, the results of the feature-selection technique are filtered based, at least in part, on information gain.

Embodiments of SVM are instances of supervised learning techniques that may be applied to classification and regression problems. For binary classification, a set of binary labeled data points (training data or examples) is provided. SVMs may be used to determine an optimal separation boundary, defined by the biological variables and/or compound variables, between two classes of data points. A separation boundary is optimal if using it as a decision rule to classify future data points minimizes an expected classification error. For linearly separable data sets (e.g., a class of absences, which may be indicated by −1, and a class of presences, which may be indicated by +1, that may be separated from each other by a line in 2 dimensions, or a so-called hyperplane in higher dimensions), SVMs may be used to determine a maximal margin hyperplane. For the maximal margin hyperplane, a linear decision boundary may be positioned such that it separates both classes and such that the distance to the closest point from each class is maximized. For non-linearly separable data sets, some training data points may be allowed on the opposite or 'wrong' side of the hyperplane, e.g., a classification error on the training data set may be allowed and may be minimized, while the margin, measured between points on the 'correct' side of the hyperplane, may be maximized.

If a linear decision boundary is not sufficiently complicated to model the separation between classes accurately, the corresponding linear model may be transformed into a non-linear model by non-linearly transforming the biological variables and/or compound variables into a possibly higher dimensional Euclidean space. A linear decision boundary constructed in such a higher dimensional Euclidean space may correspond to a non-linear decision boundary in the original space of biological variables and/or compound variables. This approach is referred to as kernel SVM.

Depending on how the margin and training error are measured, and how a trade-off between maximizing the margin and minimizing the training error is established, different types of SVMs may be obtained. In some embodiments, SVM may include standard 1-norm SVM (measuring the margin using Euclidean distance, i.e., a $L_2$-norm, and the training error using a $L_1$-norm), standard 2-norm SVM (measuring the margin using Euclidean distance, i.e., the $L_2$-norm, and the training error using the $L_1$-norm), and/or LP-SVM (measuring the margin using the $L_1$-norm and the training error using the $L_1$-norm). Each of these 3 types of SVM may be a C-type or η-type SVM. These two varieties correspond to different ways of trading-off maximizing the margin against minimizing the training error. The 1-norm SVM, standard 2-norm SVM, and/or LP-SVM may be a C+/C− or η+/ρ− type, where errors on positive (+1) labeled training data are weighted differently than errors on negative (−1) labeled training data.

The principle for binary classification described above may be extended to regression, for example, by copying the regression data twice, shifting both copies in opposite directions (over a distance epsilon) with respect to the continuous output dimension or variable and establishing a regression surface as a decision boundary between the two shifted copies that may be regarded as two classes for binary classification. As a consequence, in some embodiments, regression versions of SVMs corresponding to previously described SVMs may be used.

The decision boundary determined using one or more SVMs may be used to discriminate between presence and absence of the trait in the trait information associated with the group of life forms. For binary classification, measures of goodness for the resulting model include a prediction accuracy that is better than predicting 50% of the positive data (e.g., occurrences, which may be indicated by a +1) as positive (i.e., true positive predictions) and better than predicting 50% of the negative data (i.e., absences, which may be indicated by a −1) as negative (i.e., true negative predictions). Doing better than 50/50 corresponds to doing better than random.

CART is a non-parametric multivariate analysis technique. It involves the determination of a binary decision tree using the training set of data. Predictions based on the resulting tree may be compared to the test set of data (cross validation). A decision tree provides a hierarchical representation of the feature space in which explanatory variables are allocated to classes (such as presence or absence of the trait in the trait information) according to the result obtained by following decisions made at a sequence of nodes at which branches of the tree diverge. Branches or divisions of the tree may be chosen to provide the greatest reduction in the statistical entropy of the variables (for a classification tree based on categorical data), such as a small or zero standard deviation, or the greatest reduction in the deviation between the biological variables (and/or compound variables) and the trait being fit (for a regression tree based on quantitative data). A tree stops growing when no significant additional reduction can be obtained by division. A node that is not further sub-divided is a terminal node. It is associated with a class. A desirable decision tree is one having a relatively small number of branches, a relatively small number of intermediate nodes from which these branches diverge, terminal nodes with a non-zero number of entries, and high prediction power (correct classifications at the terminal nodes). In some embodiments, CART may be used in conjunction with a gradient boosting algorithm, where each boosted tree is combined with its mates using a weighted voting scheme. Gradient boosting may be used to force the binary decision tree to classify data that was previously misclassified.

As noted above, a wide variety of statistical analysis techniques may be used to determine the one or more statistical relationships. These may include: one or more supervised learning techniques, one or more unsupervised learning techniques, one or more parametric analysis techniques (such as a Pearson's product-moment correlation coefficient r or an inner product), and/or one or more non-parametric analysis techniques. Non-parametric analysis techniques may include: a Wilcoxon matched pairs signed-rank test (for ordinal or ranked data), a Kolmogorov-Smirnov one-sample test (for ordinal or ranked data), a dependent t-test (for interval or ratio data), a Pearson chi-square, a chi-square test with a continuity correction (such as Yate's chi-square), a Mantel Heanszel chi-square test, a linear-by-linear association test, a maximum likelihood test, a risk ratio, an odds ratio, a log odds ratio, a Yule Q, a Yule Y, a phi-square, a Kappa measure of agreement, a McNemar change test, a Mann Whitney U-test, a Spearman's rank order correlation coefficient, a Kendall's rank correlation, a Krushcal-Wallis One-Way Analysis of Variance, and/or a Turkey's quick test.

Supervised learning techniques may include: least-squares regression (including correlation), ridge regression, partial least-squares (also referred to as partial correlation), a perceptron algorithm, a Winnow algorithm, linear discriminant analysis (LDA), Fisher discriminant analysis (FDA), logistic regression (LR), a Parzen windows classifier, a (k−) nearest-neighbor classification, multivariate adaptive regression splines (MARS), multiple additive regression trees (MART), SVM, a least absolute shrinkage and selection operator or LASSO (a regularized linear regression technique like ridge regression, but with $L_1$-norm regularization of the coefficients), least angle regression (LARS), decision trees (such as CART, with and without gradient boosting, such as ID3 and C4.5), bagging, boosting (such as, adaboost) of simple classifiers, kernel density classification, a minimax probability machine (MPM), multi-class classification, multi-label classification, a Gaussian Process classification and regression, Bayesian statistical analysis, a Naive Bayes classifier, and/or neural networks for regression and classification. While some of these supervised learning algorithms are linear, it should be understood that one or more additional non-linear versions may be derived using the same 'kernel-methodology', as previously described for the SVM, leading to a spectrum of kernel-based learning methods, for example, kernel FDA, kernelized logistic regression, the kernelized perceptron algorithm, etc. One or more of these non-linear versions may be used to perform the statistical analysis.

Unsupervised learning techniques may include: a kernel density estimation (using, for example, Parzen windows or k-nearest neighbors), more general density estimation techniques, quantile estimation, clustering, spectral clustering, k-means clustering, Gaussian mixture models, an algorithm using hierarchical clustering, dimensionality reduction, principal component analysis (PCA), multi-dimensional scaling (MDS), isomap, local linear embedding (LLE), self-organizing maps (SOM), novelty detection (which is also referred to as single-class classification, such as single-class SVM or single-class MPM), canonical correlation analysis (CCA), independent component analysis (ICA), factor analysis, and/or non-parametric Bayesian techniques like Dirichlet processes. As noted above for the supervised learning techniques, one or more additional non-linear versions of one or more linear unsupervised learning techniques may be used to perform the statistical analysis, such as kernel PCA, kernel CCA and/or kernel ICA.

In some embodiments, at least a portion of the statistical analysis, such as determination of one or more statistical relationships and/or identification of one or more association variables includes spectral analysis. For example, a Fourier transform or a discrete Fourier transform may be performed on the trait information, one or more patterns of occurrence of one or more biological variables, and/or one or more patterns of occurrence of one or more compound variables. Analysis in the frequency domain may allow patterns in at least some of the data associated with the group of life forms to be determined.

In some embodiments, calculating one or more statistical relationships and/or identifying one or more association variables includes the use of design of experiments. For example, the data associated with the group of life forms may correspond to an orthogonal array.

In some embodiments, a signal-to-noise metric is used to adjust how the one or more association variables are identified. This signal-to-noise metric may be computed using the set of biological variables of the group of life forms. Based on the computed signal-to-noise metric, how the one or more association variables are identified may vary from only using the occurrence and/or interaction rankings (for low values of the signal-to-noise metric) to only using the largest values of statistical association (e.g., without the occurrence and/or interaction rankings), which may be appropriate for high values of the signal-to-noise metric. In general, for an arbitrary value of the signal-to-noise metric, the one or more association variables may be identified using a weighted combination of the occurrence and/or interaction rankings and the largest values of statistical association, where the weights $\lambda i$ of these terms may be a function of the signal-to-noise metric (for example, the weights of the two terms may be $\lambda$ and $1-\lambda$). Alternatively or additionally, such as weighted combination may be used in a modified version of a supervised learning technique, such as LASSO.

In some embodiments, the initial set of biological variables is pruned or reduced prior to identifying the one or more association variables based on known or pre-determined association variables for the trait, such as one or more genes associated with a disease that have been identified using: linkage analysis, the biochemistry of the disease, or another technique known to one of skill in the art.

We now describe embodiments of a circuit and a computer system that may perform at least a portion of the statistical analysis and/or the identifying of the one or more association variables. This circuit may contain one or more filters, including: analog filters, digital filters, adaptive filters (using, for example, a least-square error or gradient approach, such as steepest decent), and/or neural networks. The one or more filters may be implemented using one or more digital signal processors (DSPs). In some embodiments, the statistical analysis and/or the identifying of the one or more association variables are implemented in hardware, for example, using one or more application-specific integrated circuits (ASICs), and/or using software.

Figure 8A:
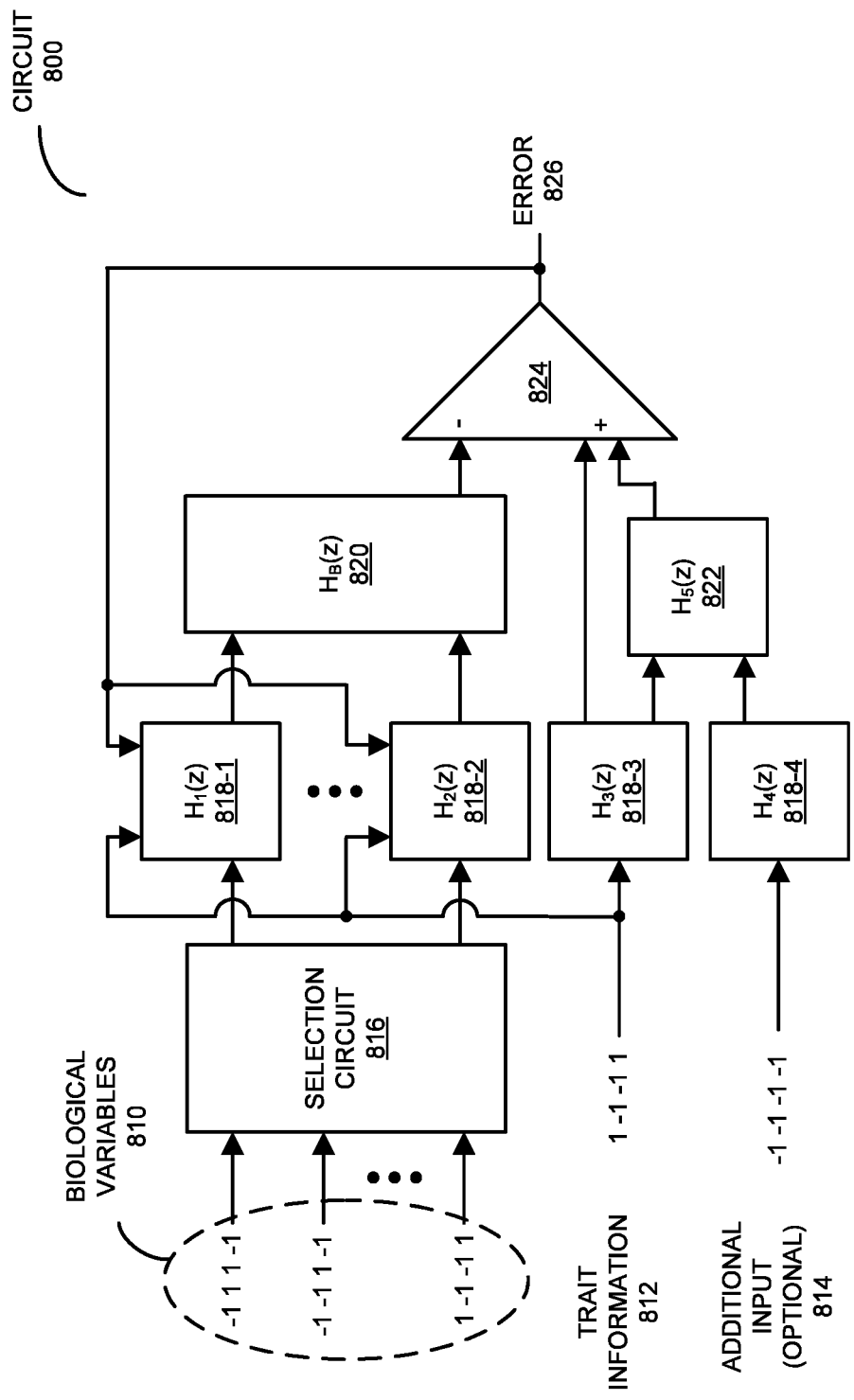
FIG. 8A is a block diagram illustrating a circuit in accordance with an embodiment of the present disclosure.

FIG. 8A presents a block diagram illustrating a circuit 800 for determining one or more statistical relationships and/or identifying one or more association variables. Presence (coded with 1s) and absence information (coded with −1s) for one or more biological variables 810 are selectively coupled using selection circuit 816 to one or more filters $H_i$ 818. Note that the selection circuit 816 may be a multiplexer. In some embodiments, filters $H_i$ 818 perform spectral modification, such as limiting or excluding one or more of the biological variables 810. Moreover, filters $H_i$ 818 may convert the presence and absence information for one or more of the biological variables 810 into one or more patterns of occurrence.

Note that filters $H_i$ 818 may be adaptive. This adaptation may be based on trait information 812 and/or an error 826. In some embodiments, the adaptation includes one or more time intervals and/or one or more offsets between these time intervals, which are used when determining compound variables. Note that the adaptation may minimize or reduce error 826 or a portion of error 826.

Outputs from one or more of the filters $H_i$ 818 may be coupled to filter $H_B$ 820. This filter may perform additional spectral modification. As a consequence, an arbitrary filtering operation may be implemented using one or more of the filters $H_i$ 818 and/or the filter $H_B$ 820. Moreover, filter $H_B$ 820 may determine a pattern of occurrence for one or more biological variables 810 and/or one or more compound variables.

Trait information 812 may be filtered using filter $H_3$ 818-3. Comparisons between an output of filter $H_3$ 818-3 and an output of the filter $H_B$ 820 may be performed using statistical analysis element 824. In some embodiments, the statistical analysis element 824 may be a comparator. Statistical analysis element may implement one or more statistical analysis techniques, such as the log-likelihood ratio. Moreover, the statistical analysis element 824 may generate error 826. Note that error 826 may be: a scalar, a vector, and/or a matrix. In some embodiments, statistical analysis element 824 may perform a relative time shifting of the output of filter $H_3$ 818-3 and the output of the filter $H_B$ 820.

In an exemplary embodiment, statistical analysis element 824 calculates one or more statistical relationships between the trait information 812 and one or more patterns of occurrence of one or more compound variables. The one or more statistical relationships may be determined sequentially and/or substantially concurrently. Note that error 826 may correspond to the one or more statistical relationships.

In some embodiments, one or more optional additional inputs, such as optional additional input 814, is filtered using one or more filters, such as filter $H_4$ 818-4, and/or combined with trait information 812 using a filter, such as filter/combiner $H_5$ 822. An output from filter/combiner $H_5$ 822 may be included in the analysis performed by statistical analysis element 824. The one or more optional additional inputs may allow inclusion of cross-terms. In some embodiments, the one or more optional additional inputs may include other disease symptoms, other diseases (such as diseases that have a comorbidity with a trait), and/or environmental factors.

While a single output is shown for the filter $H_B$ 820, there may be additional outputs that are used by statistical analysis element 824. Similarly, there may be additional outputs from filter/combiner $H_5$ 822 that are used by statistical analysis element 824. While embodiment 800 uses presence and absence information in the one or more biological variables 810, trait information 812, and optional additional input 814, in some embodiments one or more of these items may only use presence information or may use only absence information. Alternatively or additionally, expression and/or suppression information may be used.

A more general description of a circuit to identify the one or more association variables is shown in FIG. 8B, which presents a block diagram illustrating circuit 850. In this circuit, biological variables 810 and trait information 812 are received by statistical computation circuit 860, which calculates the statistical relationships. (In some embodiments, one or more optional additional inputs, such as optional additional input 814 in FIG. 8A, are also received and used in the analysis.) Then, ranking circuit 862 determines the occurrence ranking of the number of occurrences of the biological variables 810 in the subset of the compound variables and/or the numbers of different mathematical interactions used to determine the compound variables in the subset of the compound variables for biological variables 810 that are associated with the corresponding numbers of occurrences, and analysis circuit 864 identifies the one or more association variables 866 based on the rankings (such as portion 718 in FIG. 7A which is substantially or approximately stable).

Circuits 800 (FIG. 8A) and 850 may include fewer components or additional components. Moreover, two or more components may be combined into a single component and/or a position of one or more components may be changed. In some embodiments the functionality of circuits 800 (FIG. 8A) and 850 is implemented more in hardware and less in software, or less in hardware and more in software, as is known in the art.

Devices and circuits described herein may be implemented using computer-aided design tools available in the art, and embodied by computer-readable files containing software descriptions of such circuits. These software descriptions may be: behavioral, register transfer, logic component, transistor and/or layout geometry-level descriptions. Moreover, the software descriptions may be stored on non-transitory computer-readable storage media.

Data formats in which such descriptions may be implemented include, but are not limited to: formats supporting behavioral languages like C, formats supporting register transfer level (RTL) languages like Verilog and VHDL, formats supporting geometry description languages (such as GDSII, GDSIII, GDSIV, CIF, and MEBES), and other suitable formats and languages. Note that physical files may be implemented on machine-readable media such as: 4 mm magnetic tape, 8 mm magnetic tape, 3½ inch floppy media, CDs, DVDs, and so on.

In some embodiments, the identification technique is used to perform feature extraction or feature selection in a multi-dimensional feature space. In particular, a computer system (such as computer system 900 in FIG. 9) may include one or more computation devices that perform computations or computer operations. For example, the one or more computation devices may include one or more of: a processor, a core in a second processor, a graphical processing unit (GPU) and another type of device configured for computation. Moreover, the computer system may include memory that stores program instructions, such as a program module.

When executed by the one or more computation devices, the program instructions cause the computer system to perform one or more operations. In particular, the computer system may optionally access a set of genetic features for individuals in a group of individuals and associated trait information, where a number of genetic features may be larger than a number of individuals. For example, the set of genetic features may be accessed in the memory, which may be local memory and/or memory that is located at a remote location from the computer system. Note that the set of genetic features may include: genetic features associated with deoxyribonucleic acid, genetic features associated with ribonucleic acid, genetic features associated with epigenetic information, genetic features associated with one or more proteins, and/or another type of biological marker.

Then, as discussed previously, the computer system may determine statistical associations (such as LLRs) between combinations of the genetic features for the individuals in the group and the trait information. Moreover, as discussed previously, the computer system may select a subset of genetic features in the set of genetic features based on one or more aggregate properties of at least a subset of the combinations, where the one or more aggregate properties include numbers of occurrences of the genetic features in the at least the subset of the combinations.

Note that a number of combinations may be larger than the number of genetic features, the selecting may involve an underdetermined problem in which a ratio of the number of the combinations to the number of the individuals is larger than a predefined value and p-values associated with the selected subset of genetic features (i.e., for a given genetic features in the subset of genetic features, a probability of statistical association of a particular value or more extreme) may be less than a second predefined value. For example, the combinations may include some or all of the pairwise combinations of the genetic features. Thus, in some embodiments, the number of combinations is the square of the number of genetic features. However, in other embodiments, the number of combinations is, at least, significantly larger than the number of features, such that the predefined value is 10, 100, 1000, $10^4$, $10^5$, $10^6$, $10^7$, $10^8$, $10^9$ or more. Moreover, the second predefined value may be 0.05, 0.01, $10^{-3}$, $10^{-8}$, $10^{-10}$, $10^{-12}$, $10^{-14}$, etc. Alternatively, the second predefined value may be less than a p-value that includes a Bonferroni correction that is based on the number of combinations. For many datasets, the feature-selection technique may identify the subset of genetic features while existing feature-selection or supervised-learning techniques (such as single-locus chi-square, Logistic regression, LASSO, SVM, CART, etc.) are unable to identify genetic features with statistical significance (which is sometimes referred to as 'significance') without increasing the number of individuals and/or reducing the number of genetic features in the set of genetic features (i.e., without reducing the severity or degree of the underdetermined problem). Consequently, the feature-selection technique may improve the ability of the computer system to identify the subset of genetic features in underdetermined problems, while, for a given dataset, using reduced system resources (such as computation cycles, memory, etc.) and/or providing improved significance relative to existing feature-selection or supervised-learning techniques. In particular, the feature-selection technique may identify the subset of genetic features with smaller p-values (by many orders of magnitude) in datasets with 10-100× fewer individuals than existing feature-selection or supervised-learning techniques. However, in other embodiments, the feature-selection technique is used for a determined or an overdetermined problem, such as a dataset in which the number of features is less than or equal to the number of observations.

In some embodiments, the computer system optionally provides a predictive model based at least on the subset of genetic features, the trait information and a supervised-learning technique, where the predictive model provides a recommendation or recommendation value for a therapeutic intervention for an individual based on at least some of the subset of genetic features. For example, the recommendation may be categorical (such as 'yes', i.e., to have or to use the therapeutic intervention, 'no', i.e., not to have or use the therapeutic intervention, or 'seek additional professional consultation' when the p-value, the accuracy or the confidence interval of the recommendation is insufficient, e.g., greater than 1% of 5%) and/or the recommendation value may have a range of 0 to 1, where values greater than a threshold value (such as 0.4 or 0.5) correspond to 'yes', values less than a second threshold value (such as 0.5 or 0.6) correspond to 'no', and values between the threshold value and the second threshold value (such as 0.4 and 0.6) correspond to 'seek additional professional consultation.'

Thus, the predictive model may be used to guide individual-specific treatment (as opposed to treatment based on the average behavior of a group), which is sometimes referred to as 'precision medicine' or 'personalized medicine.' The predictive model may recommend: a prescription medicine approved by a regulatory agency (such as the FDA) for a medical condition or an off-label medical condition, a dosage or frequency of use of the prescription medicine (such as a dosage or a frequency within a range of those used for a particular prescription medicine), an over-the-counter medicine, a dosage or frequency of use of the over-the-counter medicine, a surgical procedure (such as a joint replacement, an invasive cardiology procedure, an appendectomy, a breast biopsy, a carotid endarterectomy, cataract surgery, a Cesarean section, a cholecystectomy, a coronary artery bypass, debridement, dilation and curettage, a skin graft, a hemorrhoidectomy, a hysterectomy, a hysteroscopy, inguinal hernia repair, low back pain surgery, a mastectomy, a partial colectomy, a prostatectomy, a releasing of peritoneal adhesions, a tonsillectomy, etc.), a diagnostic technique (such as a type of medical imaging, e.g., X-ray, ultrasound, MRI, etc.), a type of medical test (such as a blood test, a urine test, a genetic test, etc.), physical therapy, and/or psychological therapy or counseling (such as psychotherapy, cognitive behavioral therapy, dialectic behavioral therapy, etc.). For example, the predictive model may recommend one or more antidepressants, one or more dosages and one or more frequencies of use, such as: Buproprion with a dose between 150-450 mg per day (e.g., 300 mg), Citalopram with a dose between 20-40 mg per day (e.g., 40 mg), Lexapro with a dose between 10-20 mg per day (e.g., 10 mg), Sertraline with a dose between 25-200 mg per day (e.g., 50 mg), Fluoxetine with a dose between 20-80 mg per day (e.g., 60 mg), Duloxetine with a dose between 20-120 mg per day (e.g., 60 mg), Venlafaxine with a dose between 75-375 mg per day (e.g., 150 mg), a medication that impacts Norepinephrine, a medication that impacts Dopamine, a medication that impacts another neurotransmitter, another Selective Serotine Reuptake Inhibitor, etc.

Note that the computer system may optionally generate the predictive model, such as using random forests or recursive feature elimination and/or bootstrapping, along with a supervised-learning technique (such as LASSO, SVM, a kernel method, Logistic regression, ridge regression, a regression technique, a classification technique, a Bayesian technique, a neural network, etc.). For example, the subset of genetic features may be used to determine a seed set of features for use when training the predictive model. In some embodiments, the seed set includes the genetic features in the subset of genetic features in isolation and the dominant or top-N (where N is an integer) LLR pairs or combinations with the genetic features in the subset of genetic features. Because the combinations may be correlated with each other (ideally, they may be step functions that match or mirror the trait), the supervised-learning technique may be suited for use with correlated features. In some embodiments, the feature selection may be coarse (i.e., with modest information gain in a very large number of combinations or a high-dimensional feature space). Consequently, the subset of genetic features may include some false positives. These false positives may be eliminated when the predictive model is generated (i.e., the supervised-learning technique may have higher information gain, but may work with a smaller feature space). Thus, the feature-selection technique is used for a first pass or initial feature selection, followed by a second pass using the results of the feature-selection technique (the subset of the genetic features) and the supervised-learning technique. As noted previously, in some embodiments the second pass may include filtering based, at least in part, on information gain of the results of the first pass.

Moreover, the computer system may optionally generate combinations of the genetic features for the individuals in the group. For example, as discussed previously the generating involves a set of mathematical operations, which may include nonlinear mathematical operations. In particular, the set of mathematical operations may be used to computer pairwise combinations of the set of genetic features. Furthermore, as discussed previously, the one or more aggregate properties may include numbers of occurrences of mathematical operations in the set of mathematical operations. Note that the numbers of occurrences of mathematical operations in the set of mathematical operations may be used to empirically determine p-values for the genetic features in the subset of genetic features. In particular, a p-value may be based on the number of occurrences of a particular genetic feature in the subset of the combinations to the power of the numbers of occurrences of mathematical operations in the subset of the combinations. This value may be multiplied by a difference of a total number of possible occurrences of the genetic feature minus the number of occurrences of a particular genetic feature to the power of the total number of mathematical operations in the set of mathematical operations minus the numbers of occurrences of mathematical operations. Next, this value may be multiplied by a binomial coefficient for n choose k, where n is the total number of mathematical operations and k is the numbers of occurrences of mathematical operations. While the preceding discussion illustrated generating the combinations using the set of mathematical operations, a variety of techniques may be used in other embodiments, such as: a Bayesian technique, multiplying pairs of genetic features, determining joint probabilities of pairs of genetic features, etc.

Note that the generating may leverage the noise in the set of features to boost sub-threshold features (such as those that have weak statistical associations in isolation or a single genetic features) above a detection threshold (such as statistical significance). Thus, the feature-extraction technique may, in part, involve Stochastic resonance, and the one or more aggregate properties may be used as a form of sharp filtering that overcomes or addresses the extreme multiple testing that occurs when the number of combinations is large. In addition, the feature-selection may also use at least the number of occurrences of the genetic features in the subset of the combinations to identify nodes in a graph of interacting genetic features, which may constitute a form of topological data mining. Once the nodes have been determined, the remainder of the graph can be determined by the computer system.

Furthermore, in some embodiments the computer system optionally identifies a noise floor, and the subset of genetic features may be included in the combinations above the noise floor. For example, as described previously the noise floor may be identified based on the one or more aggregate properties of different subsets of the combinations. However, a wide variety of techniques may be used to identify the noise floor, such as by comparing the subset of genetic features identified in subsets of the combinations for the trait versus the subset of the features that are identified in subsets of the combinations for a pseudorandom or a random trait. In some embodiments, the noise floor is identified based, at least in part, on a difference between autocorrelations of one or more of the genetic features and cross-correlations of the one or more of the genetic features.

Additionally, the subset of the combinations may have statistical associations that are larger than a threshold value. For example, the subset of the combinations that are above the noise floor may include those combinations that have statistical associations (such as LLRs) greater than 9, 12, 15, etc. However, in other embodiments, instead of using the subset of genetic features that are included in the combinations above the noise floor, the subset of genetic features may be included in the combinations that have the largest statistical associations, such as the top-N LLRs (where N is an integer, e.g., the top 100, the top 1000, the top 3000, the top 10,000, etc.). Thus, the one or more aggregate properties may include the number of occurrences of the genetic features in the combinations having the top-N or the largest statistical associations.

Instead of performing the feature selection, in other embodiments a computer may be used to initiate the feature selection by a computer system at a remote location. In particular, the computer (such as computer system 900 in FIG. 9) may include one or more computation devices that perform computations or computer operations. For example, the one or more computation devices may include one or more of: a processor, a core in a second processor, a GPU and another type of device configured for computation. Moreover, the computer may include memory that stores program instructions, such as a program module.

When executed by the one or more computation devices, the program instructions cause the computer to perform one or more operations. In particular, the computer may provide, via an interface circuit, instructions for analysis by the computer system of the set of genetic features for the individuals in the group of individuals and the associated trait information, where the number of genetic features may be larger than the number of individuals. Note that the instructions may include information specifying a location of the set of genetic features for the individuals in the group and the trait information, such as in the memory and/or in memory at a remote location from the computer and/or the computer system. Alternatively or additionally, the instructions may include the set of genetic features for the individuals in the group and the trait information.

Then, the computer may receive, via the interface circuit, the subset of genetic features in the set of genetic features based on the one or more aggregate properties of at least the subset of the combinations, where the one or more aggregate properties include the numbers of occurrences of the genetic features in the at least the subset of the combinations. Note that the number of combinations may be larger than the number of genetic features, the selecting may involve an underdetermined problem in which the ratio of the number of the combinations to the number of the individuals is larger than the predefined value and the p-values associated with the selected subset of genetic features may be less than the second predefined value.

In some embodiments, instead of or in addition to the subset of genetic features, the computer may receive, via the interface circuit, the predictive model in response to providing the instructions for the analysis. The predictive model may be based at least on the subset of genetic features in the set of genetic features, the trait information and the supervised-learning technique, where the subset of genetic features corresponds to the one or more aggregate properties of at least the subset of combinations of the set of genetic features. Moreover, the one or more aggregate properties may include the numbers of occurrences of the genetic features in the at least the subset of the combinations, and the predictive model may provide the recommendation or the recommendation value for the therapeutic intervention for the individual based on at least the subset of genetic features.

Similarly, in some embodiments the computer system (such as computer system 900 in FIG. 9) may include one or more computation devices that perform computations or computer operations, and which are sometimes referred to as 'processing circuits'. For example, the one or more computation devices may include one or more of: a processor, a core in a second processor, a GPU and another type of device configured for computation. Moreover, the computer system may include memory that stores program instructions, such as a program module.

When executed by the one or more computation devices, the program instructions cause the computer system to perform one or more operations. In particular, the computer system may receive the instructions for the analysis by the computer system of the set of genetic features for the individuals in the group of individuals and the associated trait information, where the number of genetic features is larger than the number of individuals. Then, the computer system may perform the analysis. Next, the computer system may provide the subset of genetic features in the set of genetic features based on the one or more aggregate properties of at least a subset of the combinations, where the one or more aggregate properties include the numbers of occurrences of the genetic features in the at least the subset of the combinations. Note that the number of combinations may be larger than the number of genetic features, the selecting may involve an underdetermined problem in which the ratio of the number of the combinations to the number of the individuals is larger than the predefined value and p-values associated with the selected subset of genetic features may be less than the second predefined value.

Alternatively or additionally, the computer system may provide, via the interface circuit, the predictive model in response to receiving the instructions for the analysis. The predictive model may be based at least on the subset of genetic features in the set of genetic features, the trait information and the supervised-learning technique, where the subset of genetic features corresponds to the one or more aggregate properties of at least the subset of combinations of the set of genetic features. Moreover, the one or more aggregate properties may include the numbers of occurrences of the genetic features in the at least the subset of the combinations, and the predictive model may provide the recommendation or the recommendation value for the therapeutic intervention for the individual based on at least the subset of genetic features.

In some embodiments, instead of using combinations of the set of genetic features, the feature-selection technique generates the combination using pairs of the set of genetic features and a set of noise vectors (such as random or pseudorandom noise vectors), which may have a common length with the genetic features in the set of genetic features. For example, a given pair may combine one of the genetic features (e.g., with values of genotype information for a locus in the genome of an individual) with one of the noise vectors. Note that the number of genetic features in the set of genetic features may be the same as, smaller than or larger than a number of noise vectors in the set of noise vectors. However, the number of entries in each of the noise vectors may be the same as the number of entries in the genetic features (i.e., the number of individuals). Thus, the feature-selection technique may use Stochastic resonance. However, as discussed previously, in order to overcome the extreme multiple testing, the feature-selection technique may use the one or more aggregate properties of a subset of the combinations to identify the subset of the genetic features. Note that the mean or average amplitude of the set of noise vectors may be selected to maximize the likelihood of correctly selecting the subset of the genetic features. For example, in datasets with known associations for a trait, the mean or average amplitude of the set of noise vectors may be selected to maximize the true positive rate in the subset of the genetic features and/or to minimize the false positive rate in the subset of the genetic features. Alternatively or additionally, the mean or average amplitude of the set of noise vectors may be selected based on a statistical characteristic of the set of genetic features, such as based on: a first standard deviation of genotype information about mean or average values for frequency of occurrence of homozygote or heterozygote markers, a second standard deviation of genotype information about mean or average values for repeated adjacent values of homozygote or heterozygote markers in a given genetic feature, a function of the first standard deviation (such as the square), a function of the second standard deviation (such as the square), another statistical moment associated with the set of genetic features, another statistical characteristic (such as a root-mean-square value), etc. Note that the noise vectors may include white noise with an approximately constant power spectral density as a function of spatial frequency (such as with 1, 5, 10 or 25% variation about a constant value) or colored noise having a power spectral density that approximately matches the power spectral density of the set of genetic features (such as 1, 5, 10 or 25% difference in power spectral density). In other embodiments, the noise vectors are random, but have mean frequencies of categorical values that match those of the set of biological variables, e.g., the same mean frequencies of '0', '1' and '2' values).

Therefore, in some embodiments, an electronic device (such as a computer system or a circuit) may select a subset of features. This electronic device may calculate combinations of features and noise vectors, where a given combination corresponds to a given feature and a given noise vector. For example, the combinations may be determined based at least in part on mathematical operations, where the given combination is based at least in part on a given mathematical operation. In particular, the given combination may be determined based at least in part on the given feature, the given mathematical operation and the given noise vector. In some embodiments, the given mathematical operation is a matrix having a number of rows and/or a number of columns equal to a number of categorical values in the given feature and the given noise vector (such as 3×3 binary-valued matrices when there are three categorical values), and when determining the given combination, the given mathematical operation is used as a look-up table with the entries in the given mathematical operation specified by given values of the categorical variables in the entries in the given feature and the given noise vector. Note that the mathematical operations may be selected such that, for a feature that includes random values, the given combination are statistically likely (such as the top-N mathematical operations, where N is an integer) to mostly closely match the types of events (such as '1's for occurrence of an event and '0' for non-occurrence or absence of the event).

Then, the electronic device may determine statistical associations (such as LLRs) between information specifying types of events and the combinations, where a given statistical association corresponds to the types of events and a given combination.

Moreover, the electronic device may identify a noise threshold associated with the combinations (e.g., as an ensemble or as a group). For example, the noise threshold may be identified based at least in part on stability of rankings associated with at least a pair of subsets of the combinations having statistical associations equal to or greater than the noise threshold, in which a given ranking is based at least in part on a first aggregate property of the given subset of the combinations. Note that the first aggregate property may be the same as or different from a second aggregate property described below. Thus, in some embodiments, the first aggregate property may be the second aggregate property. Alternatively or additionally, the noise threshold may be identified based at least in part on between autocorrelations and cross-correlations of the combinations having the statistical associations equal to or greater than the noise threshold. The former may correspond to a mean signal energy or power in the features, while the latter may correspond to a mean noise energy or power in the features. The noise threshold may be identified when the difference exceeds a predefined value, such as 0 dB, 10 dB, 20 dB, 30 dB, etc.

Next, for a group of combinations having statistical associations equal to or greater than the noise threshold, the electronic device may select the subset of the features based at least in part on the second aggregate property of the group of combinations, where the second aggregate property includes numbers of occurrences of the features in the group of combinations. In some embodiments, the subset of the features is selected based at least in part on a third aggregate property, where the third aggregate property includes numbers of occurrences of the mathematical operations for the features in the group of combinations. Alternatively, the group of combinations may include the top-M statistical associations (where M is an integer, such as the top-300 statistical associations), and the subset of the features is selected based on the second aggregate property or the third aggregate property.

Moreover, the features may include at least one of: genetic features, environmental features, features associated with one or more electronic medical records, or features associated with insurance records. In some embodiments, the genetic features include at least one of: features associated with deoxyribonucleic acid, features associated with ribonucleic acid, features associated with epigenetic information, features associated with one or more proteins, or features associated with another type of biological marker.

Furthermore, the types of events may include the occurrence and the absence of the event. Alternatively or additionally, the types of events may include at least one or more of: occurrence and absence of a trait, different medical outcomes (such as living or dying), responses to a first type of treatment (such as a top-25 or 50% of responders and a bottom-25 or 50% of responders, occurrence or absence of a side effect, etc.), states of an episodic medical condition (such as presence of absence of a migraine attack or an epileptic seizure, presence of absence of cancer, etc.), or costs associated with a second type of treatment. Based on such events (which, in some embodiments, may be binary valued), the feature-selection technique may be used to improve outcomes, reduce costs, identify responders to a treatment (such as a medication), etc.

Moreover, the features may be associated with one of: an individual, or a group of individuals. Thus, the feature-selection technique may be used on an individual basis (such as for multiple instances of the types of events) or for a population (who have multiple instances of the types of events).

As noted previously, the noise vectors may include random or pseudorandom numbers having mean amplitudes corresponding to a statistical characteristic of the features. Moreover, mean frequencies of occurrence of categorical variables in the noise vectors may approximately match (such as within 1, 5 or 10% of) mean frequencies of occurrence of the categorical variables in the features.

In some embodiments, the electronic device generates a predictive model based at least in part on the subset of features, the types of events and a supervised-learning technique. The predictive model may provide a recommendation or a prediction based at least in part on values for the subset of the features (which are used as inputs). For example, the predictive model may recommend a treatment or a therapy. Alternatively, the predictive model may predict a value for one of the types of events. In this way, the predictive model may be used to predict occurrence of a trait, such as a disease (e.g., heart failure).

In some embodiments, at least some of the operations performed by the electronic device are performed by a cloud-based computer, and at least some of the operations performed by the electronic device are performed by a local client. For example, the local client may provide information the specifies the features, the types of events, the mathematical operations, the aggregate properties, other run or operational parameters, etc. Then, the cloud-based computer may perform the feature-selection technique and may report back the selected subset of the features and/or the predictive model. The selected subset of the features may reflect (i.e., may have characteristics of) the group of features and/or the identified noise threshold.

In some embodiments, instead of repeating the feature-selection technique multiple times using a random or pseudorandom noise vector instead of the trait, and then averaging and subtracting the identified ranking (or the subset of the genetic features) off from the subset of the genetic features that is identified when the trait is used in the feature-selection technique, the expectation value in the LLR calculation may be modified to correct for the background. For example, the expectation value may vary for different mathematical operations. The expectation values may be determined using a random dataset that has the same frequencies or distribution of values for the set of genetic features (such as mean categorical values that match those of the set of biological variables, e.g., the same mean '0', '1' and '2' values). These expectation values and the associated mathematical operations may be stored in a look-up table. Then, when calculating the statistical association between the trait and a particular pair of genetic features or a pairing of a genetic feature and a noise vector, the look-up table may be used to determine the appropriate expectation value based on the mathematical operation that was used to generate the pair.

In some embodiment, the set of features is preprocessed to reduce or eliminate spurious or extrinsic effects prior to the feature-selection technique. For example, with the set of genetic features, the preprocessing may include one or more operations. These one or more operations may be based, at least in part, on Anderson et al., "Data quality control in genetic case-control association studies", Nature Protocol, September 2010, 5(9), 1567-1573. In particular, the one or more preprocessing operations may include a sex check (for consistency). Then, an operation for heterozygosity/missing data may be performed. In particular, individuals that are more than ±2 or ±3 standard deviations from the mean heterozygosity rate (depending on the distribution of the data) may be rejected, and subjects having more missing data than a missingness threshold at +2 or +3 standard deviations may be rejected. Moreover, related individuals may be rejected. In particular, pairs of individuals whose identity by descent (IBD) is greater than 0.185 (which is between the second and third generations) may be rejected.

Next, the one or more preprocessing operations may include divergent ancestry. In this operation, there may not be a fixed criterion. Instead eigenvector plots in principal component analysis may be used to screen for outliers. In some embodiments, genetic markers for known ancestral subpopulations (such as European, African or Han) are 'injected' or added to a dataset, and individuals that are not grouped or clustered near one of the known ancestral subpopulations are removed.

Furthermore, differing genotype call rate may be screened. In particular, genetic features or markers having p-values for the difference in the genotype call rate between cases and controls that are less than $10^{-5}$ may be discarded.

Additionally, Hardy-Weinberg Equilibrium may be checked. In particular, genetic features or markers may be dropped if their p-values are less than $10^{-5}$.

Moreover, the one or more preprocessing operations may include genotype rate. In particular, a genetic feature or marker may be dropped if the genotyping rate is less than 95%.

Then, the minor allele frequency may be checked. In particular, a genetic feature or marker may be dropped if the minor allele frequency is less than 0.01. Thus, the feature-selection technique may be used with common variations. However, in other embodiments the feature-selection technique is used with rare variations (minor allele frequencies less than 0.01).

Next, a correction or check for global population stratification may be performed using, e.g., multi-dimensional scaling (MDS).

Furthermore, the set of features may be corrected for linkage disequilibrium using, e.g., tagging. In particular, the tagging may use a value of $r^2$ of 0.4. Note that the genetic features or markers may be sorted or processed per chromosome, i.e., linkage disequilibrium may be checked intra-chromosome.

Additionally, the set of features may be checked for admixture. Genetic features that are likely affected by admixture (based on proximate genetic features associated with the ancestral subpopulations) may be removed before the feature-selection technique or flagged so that such results are excluded from the subset of the genetic features. In this way, a local population stratification correction may be applied to the set of genetic features. Alternatively or additionally, admixture effects may be included or considered when the statistical associations (such as the LLRs) are calculated during the feature-selection technique.

In some embodiments, the set of genetic features is corrected for gender stratification. In particular, the sampling of the feature space by the combinations for the X chromosome for women may be different than for men because women have two copies of the X chromosome, while men have one copy. If there is an imbalance in the number of men and the number of women in the cases and the controls, this can cause spurious statistical associations with the trait. In order to address this issue, the number of men and the number of women in the cases and the controls may be balanced during the feature-selection technique. Alternatively, the men and the women may be analyzed separately, i.e., a run with only men in the cases and the controls, and a separate run with only women in the cases and the controls.

While the preceding discussion illustrated the feature-selection technique using the set of genetic features, in other embodiments the feature-selection technique may alternatively or additionally be applied to sets of environmental factors (such as dietary patterns, diet or foods that are consumed, ingredients in the foods that are consumed, sleep patterns, activity patterns, emotional response, behaviors, exercise, sexual patterns, weather patterns, physiological monitoring of an individual, exposure to chemicals, exposure to a stimulus, smoking, allergens, smells, light conditions, sounds, etc.). Consequently, the set of features used as inputs to the feature-selection technique may include values of environmental factors collected at a particular time or longitudinal values of a set of environmental factors that are collected at different times. Stated differently, in some embodiments the set of features includes time domain or time-sampled values. Such a time sequence may be converted into a set of features. For example, each environmental factor within a time interval in the time sequence may be a separate feature in the set of features. In this way, the samples or values of the environmental factors in multiple time intervals (which may be separate or at least partially overlapping) may be used to determine separate features in the set of features. In this way, the feature-selection technique may be extended to analyze time-domain data. In some embodiments, the genetic features and/or the environmental factors are binned into one or more time intervals (such as 0-6 hrs, 0-12 hrs, 0-24 hrs, 24-48 hrs, 48-72 hrs, etc.) preceding one or more onsets or events, such as consumption of a medication or a drug, an environmental exposure, a medical condition (such as a migraine, a stroke, an epileptic seizure, etc.), a therapeutic intervention, etc. In this way, the set of features may be defined in one or more time intervals that are synchronized to or relative to the one or more onsets.

Alternatively or in addition to genetics, the feature-selection technique may be applied to a wide variety of problems or types of data, including: information corresponding to neurological signals (such as electroencephalogram data, deep-brain signals, electromyogram data, etc.), electronic medical record data (such as a dataset summarizing patient contact with one or more medical professionals, diagnostic or therapeutic interventions, clinical trial data, hospitalization information, operational details, e.g., frequency of appointments, duration of appointments, etc.), longevity data (such as lifespan), sports data (such as athletic performance), financial data (such as stock or bond data), a neural-network training dataset, economic data (such as micro or macro-economic data), scientific data (such as in physics, materials science, chemistry, biology, geology, etc.), dating information, operations data (such as for sales, marketing, manufacturing, etc.), employee data (such as performance or retention data), recommendation data (such as advertising, mail direct-mail campaigns, search-engine information, etc.), etc. Thus, the feature-selection technique may be a general purposes technique for use in performing feature selection (i.e., general machine learning) and, in some embodiments, for undetermined problems. (However, in other embodiments the feature-selection technique may be used for determined or overdetermined problems.) Consequently, the feature selection and/or the predictive model may be used with a variety of 'traits,' such as: treatment outcome, survival (i.e., to estimate when a patient may die), side effects, cost, etc. Note that continuous features and/or traits in the data being analyzed may be discretized or quantized based on one or more thresholds. In some embodiments, the quantization is based, at least in part, on information gain.

For example, the set of features may include electronic medical records for the individuals and the trait may include an associated cost of providing a discrete instance of a service (or a set of services) that is associated with a bundled payment. Using the feature-selection technique the subset of features that are potentially predictive of the relative cost of treating the different individuals can be identified. The resulting predictive model may be used to predict the cost of treating an individual based on their electronic medical record. These predictions may be used by an insurance, a hospital, a medical or a governmental organization when determining the price of a bundled payment and/or to drive internal improvements in their procedures to reduce costs. Alternatively or additionally, the trait may include an outcome of providing the discrete instance of the service (or the set of services) that is associated with the bundled payment. For example, the outcome may include a re-admission probability, pain six months after treatment is completed, quality-of-life information, a patient satisfaction survey, survival time, the probability of a side effect, etc. Using the feature-selection technique the subset of features that are potentially predictive of the outcomes after treating the different individuals can be identified. The resulting predictive model may be used to predict the outcome of treating an individual based on their electronic medical record. These predictions may be used by the organization when determining whether or not the individual is a suitable candidate for a particular therapeutic intervention and/or to drive internal improvements in their procedures to improve outcomes.

Thus, in general, the feature-selection technique may be applied to a wide variety of types of data, such as: medical data, environmental data, non-medical data, etc.

FIG. 9 presents a block diagram illustrating a computer system 900. Computer system 900 includes: one or more processors (or processor cores) 910, a communication interface 912, a user interface 914, and one or more signal lines 922 coupling these components together. Note that the one or more processors (or processor cores) 910 may support parallel processing and/or multi-threaded operation, communication interface 912 may have a persistent communication connection, and the one or more signal lines 922 may constitute a communication bus. Moreover, user interface 914 may include: a display 916, a keyboard 918, and/or a pointer 920, such as a mouse.

Memory 924 in computer system 900 may include volatile memory and/or non-volatile memory. More specifically, memory 924 may include: ROM, RAM, EPROM, EEPROM, flash, one or more smart cards, one or more magnetic disc storage devices, and/or one or more optical storage devices. Memory 924 may store an operating system 926 that includes procedures (or a set of instructions) for handling various basic system services for performing hardware-dependent tasks. Moreover, memory 924 may also store communication procedures (or a set of instructions) in a communication module 928. These communication procedures may be used for communicating with one or more computers, devices and/or servers, including computers, devices and/or servers that are remotely located with respect to computer system 900.

Memory 924 may also include one or more program modules 930 (and, more general, program instructions), including: statistical analysis module 930 (or a set of instructions), conversion module 932 (or a set of instructions), ranking module 934 (or a set of instructions), background-correction module 936 (or a set of instructions), compound-variable generator 942 (or a set of instructions), optional signal-processing module 946 (or a set of instructions), and/or sequence generator 950 (or a set of instructions). In the present discussion, note that a 'program module' may include software or computer code (such as instructions or program instructions) that, when executed, perform at least a portion of a function or an operation, such as a at least a portion of the feature-selection technique.

Conversion module 932 may convert biological variables 938 for a group of life forms, such as biological variable A 940-1 or biological variable B 940-2, into categorical data.

In some embodiments, biological variables 938 and/or information for one or more traits 952 associated with the group of life forms are preconditioned using optional signal-processing module 946. For example, optional signal-processing module 946 may filter data and/or may perform a transform, such as: a fast Fourier transform, a Laplace transform, a discrete Fourier transform, a Z-transform, and/or any other transform technique now known or later developed.

Then, compound-variable generator 942 may determine one or more compound variables 954 using one or more mathematical interactions 958 and at least some of the biological variables 938 (for example, statistical analysis module 930 may exclude one or more of the biological variables 938 using optional haplotype map 948). Alternatively, compound variables 954 may be pre-determined. Note that in some embodiments compound variables 954 are determined using optional weights 944.

Next, statistical analysis module 930 may determine statistical relationships between a pattern of occurrence of one or more traits 952 and patterns of occurrence of at least some of the compound variables 954. (Note that statistical analysis module 930 may exclude one or more of the compound variables 954 prior to determining the statistical relationships.) Moreover, ranking module 934 may determine one or more rankings 960 of the number of occurrences of biological variables in statistically significant statistical compound variables above a noise floor. For example, the one or more rankings 960 may include one or more occurrence rankings at different statistical significance criteria and/or one or more interaction rankings.

Additionally, background-correction module 936 may determine another occurrence ranking based on statistical relationships between at least some of the compound variables 954 and a sequence of values generated using sequence generator 950. This other occurrence ranking may be subtracted from at least one of the occurrence rankings in one or more rankings 960.

Then, statistical analysis module 930 may identify one or more association variables 956 based on ranking 960 (which may include an occurrence ranking after correcting for the background). In some embodiments, the operations of the various modules are repeated to higher order, i.e., in compound variables that include additional biological variables in the biological variables 938.

Instructions in the various modules in the memory 924 may be implemented in: a high-level procedural language, an object-oriented programming language, and/or in an assembly or machine language. The programming language may be compiled or interpreted, i.e., configurable or configured, to be executed by the one or more processors (or processor cores) 910.

Although computer system 900 is illustrated as having a number of discrete components, FIG. 9 is intended to be a functional description of the various features that may be present in computer system 900 rather than a structural schematic of the embodiments described herein. In practice, and as recognized by those of ordinary skill in the art, the functions of computer system 900 may be distributed over a large number of servers or computers, with various groups of the servers or computers performing particular subsets of the functions. In some embodiments, some or all of the functionality of computer system 900 may be implemented in one or more ASICs and/or one or more DSPs.

Computer system 900 may include fewer components or additional components. Moreover, two or more components may be combined into a single component and/or a position of one or more components may be changed. In some embodiments the functionality of computer system 900 may be implemented more in hardware and less in software, or less in hardware and more in software, as is known in the art.

Figure 10:
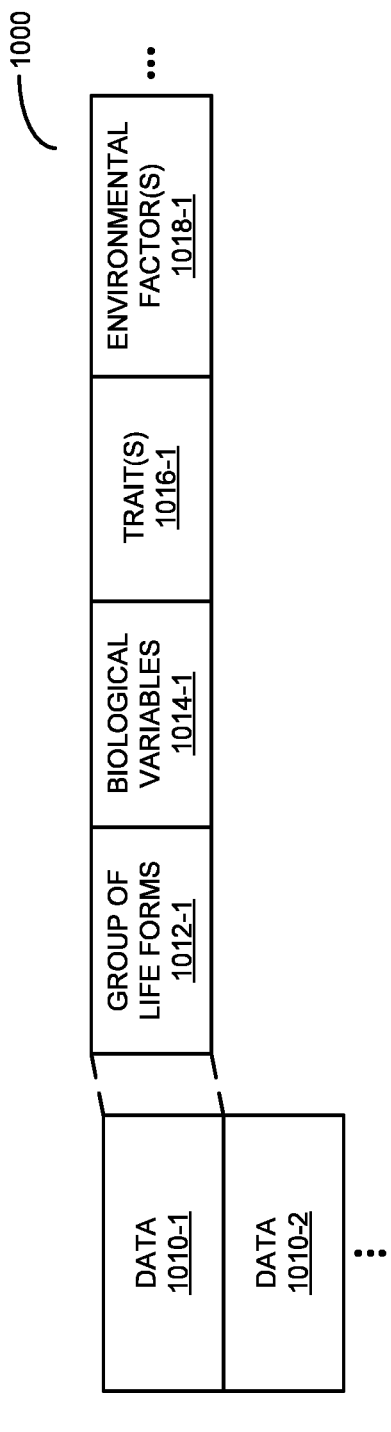
FIG. 10 is a block diagram illustrating a data structure in accordance with an embodiment of the present disclosure.

We now describe embodiments of a data structure that may be used in computer system 900. FIG. 10 presents a block diagram illustrating a data structure 1000. This data structure may include information or data 1010, such as biological variables, compound variables, and/or trait information associated with life forms in a group of life forms. For example, for data 1010-1, the information may include: group of life forms 1012-1, one or more biological variables 1014-1 associated with members of group 1012-1, information about one or more associated traits 1016-1 of the members of group 1012-1, and/or one or more environmental factors 1018-1 (which may be included with the one or more biological variables 1014-1).

Figure 11:
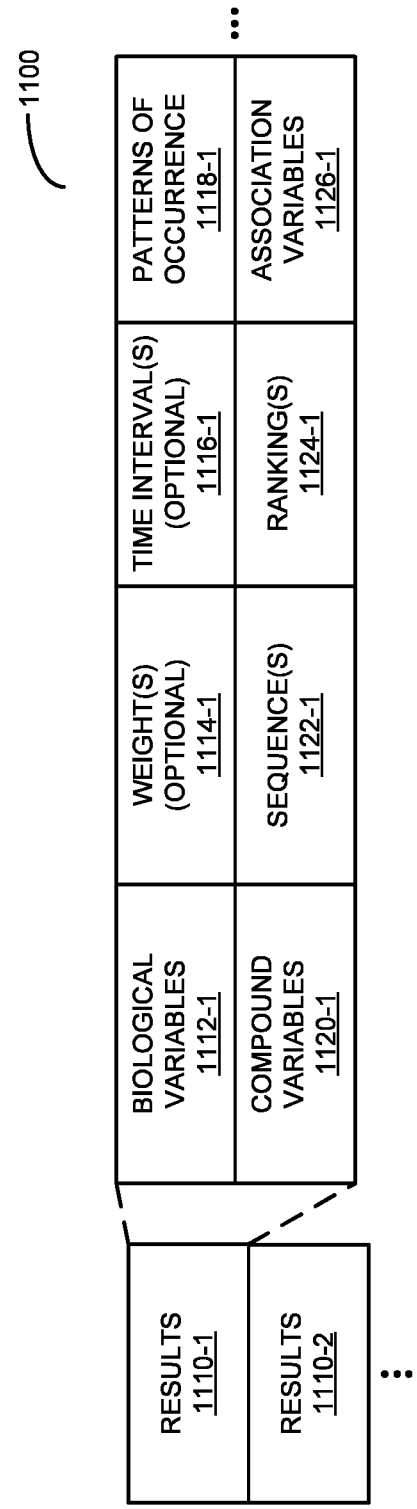
FIG. 11 is a block diagram illustrating a data structure in accordance with an embodiment of the present disclosure.

FIG. 11 presents a block diagram illustrating a data structure 1100. This data structure may include results 1110, such as statistical relationships, rankings, and/or association variables for one or more populations, such as the group of life forms, and/or one or more subsets of a given population. For example, results 1110-1 may include: one or more biological variables 1112-1, one or more optional weights 1114-1, one or more optional time intervals 1116-1, one or more patterns of occurrence 1118-1, one or more compound variables 1120-1, one or more sequences 1122-1 (such as a sequence of random or pseudorandom values), one or more rankings 1124-1 (such as one or more occurrence rankings and/or one or more interaction rankings), and/or one or more association variables 1126-1.

Note that in some embodiments of the data structures 1000 (FIG. 10) and/or 1100 there may be fewer or additional components. Moreover, two or more components may be combined into a single component and/or a position of one or more components may be changed.

While embodiments of apparatuses and related methods for identifying one or more association variables have been described, the apparatuses and related methods may be applied generally to determine statistical relationships in a wide variety of underdetermined problems in medicine, psychology, statistics, engineering, finance, applied mathematics and operations research (and, thus, in general to an arbitrary supervised learning problem). Consequently, the one or more association variables may be identified based on traits or features other than those corresponding to biological variables.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Thus, the present disclosure is not intended to be limited to the embodiments shown, but is to be accorded the widest scope consistent with the principles and features disclosed herein.

What is claimed:

1. An electronic device, comprising:
one or more processing circuits;
memory configured to store program instructions, wherein, when executed by the one or more processing circuits, the program instructions cause the electronic device to perform one or more operations comprising:
calculating combinations of feature vectors and noise vectors, wherein a given combination in the combinations corresponds to a given feature vector in the feature vectors and a given noise vector in the noise vectors, wherein a number of the feature vectors exceeds one hundred and a number of the combinations exceeds ten thousand, and wherein the number of feature vectors is at least an order of magnitude larger than a number of entries in the given feature vector;
determining statistical associations between types of events and the combinations, wherein a given statistical association in the statistical associations corresponds to the types of events and the given combination;
computing a noise threshold associated with a group of combinations in the combinations, wherein the noise threshold corresponds to a first aggregate property of the group of combinations, wherein the first aggregate property comprises numbers of occurrences of the feature vectors in the group of combinations, and wherein the group of combinations have statistical associations equal to or greater than the noise threshold;
selecting a subset of the feature vectors based at least in part on the first aggregate property of the group of combinations; and
training a supervised machine-learning model using the types of events and a training dataset that is based at least in part on the selected subset of the feature vectors, wherein training the supervised machine-learning model comprises determining parameters in the supervised machine-learning model and identifying feature vectors in the subset of feature vectors to use in the supervised machine-learning model, and wherein the supervised machine-learning model predicts the types of events based at least in part on the identified feature vectors and the parameters.

2. The electronic device of claim 1, wherein the combinations are determined based at least in part on mathematical operations; and
wherein the given combination is based at least in part on a given mathematical operation in the mathematical operations.

3. The electronic device of claim 2, wherein the subset of the feature vectors is selected based at least in part on a second aggregate property; and
wherein the second aggregate property comprises numbers of occurrences of the mathematical operations for the feature vectors in the group of combinations.

4. The electronic device of claim 1, wherein the feature vectors comprise genetic feature vectors.

5. The electronic device of claim 4, wherein the genetic feature vectors comprise feature vectors associated with deoxyribonucleic acid.

6. The electronic device of claim 1, wherein the types of events comprise instances of occurrence of an event and instances of absence of the event.

7. The electronic device of claim 1, wherein the types of events comprise responses to a first type of treatment.

8. The electronic device of claim 1, wherein the noise threshold is computed based at least in part on at least one of: stability of rankings associated with at least a pair of subsets of the combinations having statistical associations equal to or greater than the noise threshold, in which a given ranking in the rankings is based at least in part on a second aggregate property of the given subset of the combinations in the subsets of the combinations; or differences between autocorrelations and cross-correlations of the combinations having the statistical associations equal to or greater than the noise threshold.

9. The electronic device of claim 8, wherein the second aggregate property is different from the first aggregate property.

10. The electronic device of claim 1, wherein the feature vectors are associated with one of: an individual, or a group of individuals.

11. The electronic device of claim 1, wherein the noise vectors comprise random or pseudorandom numbers having mean amplitudes corresponding to a statistical characteristic of the feature vectors.

12. The electronic device of claim 1, wherein a mean of frequencies of occurrence of categorical values in the noise vectors approximately match a mean of frequencies of occurrence of the categorical values in the feature vectors.

13. The electronic device of claim 1, wherein the one or more operations comprise generating a predictive model based at least in part on the subset of feature vectors, the types of events and a supervised-learning technique; and
wherein the predictive model provides a recommendation or a prediction as an output from the predictive model based at least in part on values for the subset of the feature vectors as inputs to the predictive model.

14. A non-transitory computer-readable storage medium for use in conjunction with an electronic device, the computer-readable storage medium storing program instructions that, when executed by the electronic device, causes the electronic device to perform one or more operations comprising:
calculating combinations of feature vectors and noise vectors, wherein a given combination in the combinations corresponds to a given feature vector in the feature vectors and a given noise vector in the noise vectors, wherein a number of the feature vectors exceeds one hundred and a number of the combinations exceeds ten thousand;
determining statistical associations between types of events and the combinations, wherein a given statistical association in the statistical associations corresponds to the types of events and the given combination;
computing a noise threshold associated with a group of combinations in the combinations, wherein the noise threshold corresponds to a first aggregate property of the group of combinations, wherein the first aggregate property comprises numbers of occurrences of the feature vectors in the group of combinations, and wherein the group of combinations have statistical associations equal to or greater than the noise threshold;
selecting a subset of the feature vectors based at least in part on the first aggregate property of the group of combinations; and
training a supervised machine-learning model using the types of events and a training dataset that is based at least in part on the selected subset of the feature vectors, wherein training the supervised machine-learning model comprises determining parameters in the supervised machine-learning model and identifying feature vectors in the subset of feature vectors to use in the supervised machine-learning model, and wherein the supervised machine-learning model predicts the types of events based at least in part on the identified feature vectors and the parameters.

15. The computer-readable storage medium of claim 14, wherein the combinations are determined based at least in part on mathematical operations; and
wherein the given combination is based at least in part on a given mathematical operation in the mathematical operations.

16. The computer-readable storage medium of claim 15, wherein the subset of the feature vectors is selected based at least in part on a second aggregate property; and
wherein the second aggregate property comprises numbers of occurrences of the mathematical operations for the feature vectors in the group of combinations.

17. The computer-readable storage medium of claim 14, wherein the noise threshold is computed based at least in part on at least one of: stability of rankings associated with at least a pair of subsets of the combinations having statistical associations equal to or greater than the noise threshold, in which a given ranking in the rankings is based at least in part on a second aggregate property of the given subset of the combinations in the subsets of the combinations; or differences between autocorrelations and cross-correlations of the combinations having the statistical associations equal to or greater than the noise threshold.

18. The computer-readable storage medium of claim 17, wherein the second aggregate property is different from the first aggregate property.

19. The computer-readable storage medium of claim 14, wherein the noise vectors comprise random or pseudorandom numbers having mean amplitudes corresponding to a statistical characteristic of the feature vectors.

20. A method for selecting a subset of feature vectors, comprising:
by an electronic device:
calculating combinations of feature vectors and noise vectors, wherein a given combination in the combinations corresponds to a given feature vector in the feature vectors and a given noise vector in the noise vectors, wherein a number of the feature vectors exceeds one hundred and a number of the combinations exceeds ten thousand;
determining statistical associations between types of events and the combinations, wherein a given statistical association in the statistical associations corresponds to the types of events and the given combination;
computing a noise threshold associated with a group of combinations in the combinations, wherein the noise threshold corresponds to a first aggregate property of the group of combinations, wherein the first aggregate property comprises numbers of occurrences of the feature vectors in the group of combinations, and wherein the group of combinations have statistical associations equal to or greater than the noise threshold;
selecting a subset of the feature vectors based at least in part on the first aggregate property of the group of combinations; and
training a supervised machine-learning model using the types of events and a training dataset that is based at least in part on the selected subset of the feature vectors, wherein training the supervised machine-learning model comprises determining parameters in the supervised machine-learning model and identifying feature vectors in the subset of feature vectors to use in the supervised machine-learning model, and wherein the supervised machine-learning model predicts the types of events based at least in part on the identified feature vectors and the parameters.

* * * * *